(12) United States Patent
Osborne et al.

(10) Patent No.: US 12,053,481 B2
(45) Date of Patent: Aug. 6, 2024

(54) COMPOSITIONS AND METHODS FOR DEEP DERMAL DRUG DELIVERY

(71) Applicant: ARCUTIS BIOTHERAPEUTICS, INC., Westlake Village, CA (US)

(72) Inventors: David W. Osborne, Fort Collins, CO (US); Babak N. Tofig, Westlake Village, CA (US)

(73) Assignee: ARCUTIS BIOTHERAPEUTICS, INC., Westlake Village, CA (US)

( * ) Notice: Subject to any disclaimer, the term of this patent is extended or adjusted under 35 U.S.C. 154(b) by 0 days.

(21) Appl. No.: 18/124,906

(22) Filed: Mar. 22, 2023

(65) Prior Publication Data

US 2023/0226083 A1     Jul. 20, 2023

Related U.S. Application Data

(63) Continuation of application No. 17/527,856, filed on Nov. 16, 2021, now Pat. No. 11,628,177.

(60) Provisional application No. 63/221,349, filed on Jul. 13, 2021, provisional application No. 63/114,887, filed on Nov. 17, 2020.

(51) Int. Cl.
| | | |
|---|---|---|
| *A61K 31/585* | (2006.01) | |
| *A61K 9/00* | (2006.01) | |
| *A61K 9/107* | (2006.01) | |
| *A61K 9/14* | (2006.01) | |
| *A61K 31/519* | (2006.01) | |
| *A61K 47/20* | (2006.01) | |
| *A61K 47/24* | (2006.01) | |
| *A61K 47/34* | (2017.01) | |

(52) U.S. Cl.
CPC .......... *A61K 31/585* (2013.01); *A61K 9/0014* (2013.01); *A61K 9/107* (2013.01); *A61K 9/1075* (2013.01); *A61K 9/146* (2013.01); *A61K 31/519* (2013.01); *A61K 47/20* (2013.01); *A61K 47/24* (2013.01); *A61K 47/34* (2013.01)

(58) Field of Classification Search
CPC .................................... A61K 31/585
USPC ........................................ 514/175
See application file for complete search history.

(56) References Cited

U.S. PATENT DOCUMENTS

| | | |
|---|---|---|
| 8,003,690 B2 | 8/2011 | Vergnault et al. |
| 9,114,077 B2 | 8/2015 | Petersen |
| 9,422,300 B2 | 8/2016 | Sun et al. |
| 9,527,851 B2 | 12/2016 | Zhang et al. |
| 9,636,353 B2 | 5/2017 | Mittal et al. |
| 9,713,590 B2 | 7/2017 | Mittal et al. |
| 10,023,577 B2 | 7/2018 | Sun et al. |
| 10,150,770 B2 | 12/2018 | Sun et al. |
| 10,428,074 B2 | 10/2019 | Zhang et al. |
| 10,786,507 B2 | 9/2020 | Lu et al. |
| 2006/0159638 A1 | 7/2006 | Segura et al. |
| 2013/0072512 A1 | 3/2013 | Jahagirdar et al. |
| 2016/0279152 A1 | 9/2016 | Chen et al. |
| 2016/0361381 A1 | 12/2016 | Green et al. |
| 2017/0020896 A1 | 1/2017 | Kelidari et al. |
| 2017/0044171 A1 | 2/2017 | Zhang et al. |
| 2019/0060311 A1 | 2/2019 | Shanler et al. |
| 2020/0276109 A1 | 9/2020 | Xi et al. |

FOREIGN PATENT DOCUMENTS

| | | |
|---|---|---|
| CN | 111278466 A | 6/2020 |
| EP | 0479777 A1 | 4/1992 |
| EP | 3714887 A1 | 9/2020 |
| WO | 9011077 A1 | 10/1990 |
| WO | 1990011077 A1 | 10/1990 |
| WO | 2019040706 A1 | 2/2019 |
| WO | 2019236596 A1 | 12/2019 |

OTHER PUBLICATIONS

Noaimi et al., "Treatment of Acne Vulgaris by Topical Spironolactone Solution Compared With Clindamycin Solution", Cureus, 13(8): e17606 (2021).
Ferreira-Nunes et al. "Follicular-targeted delivery of spironolactone provided by polymeric nanoparticles", Colloids and Surfaces B: Biointerfaces. 208: 112101 (2021).
International Preliminary Report on Patentability and Written Opinion of the International Searching Authority, issued in corresponding International Application No. PCT/US2021/059487, dated May 16, 2023, 7 pages.
Non-Final Office Action issued in corresponding U.S. Appl. No. 17/984,405, dated Jul. 10, 2023, 16 pages.
Harvey et al. "MALDI-MSI for the Analysis of a 3D Tissue-Engineered Psoriatic Skin Model"; Proteomics 2016, 16, 1718-1725:2016.
International Search Report and the Written Opinion of the International Searching Authority, issued in corresponding International Application No. PCT/US2021/059487, dated Mar. 4, 2022, 14 pages.
International Search Report and the Written Opinion of the International Searching Authority, issued in corresponding International Application No. PCT/US2021/059479, dated Mar. 11, 2022, 18 pages.
MinoxidilMax, "Topical Spironolactone 5% for Hair Loss, Acne," printed on Feb. 22, 2022, X055894342, retrieved from the Internet: https://www.minoxidilmax.com/topical-spironolactone, 6 pages.

(Continued)

*Primary Examiner* — Taofiq A Solola
(74) *Attorney, Agent, or Firm* — Rothwell, Figg, Ernst & Manbeck, P.C.

(57) ABSTRACT

Pharmaceutical compositions for the topical administration of a drug to the pilosebaceous unit and methods for administering the same. As disclosed herein, the inventors of the present invention have made the surprising discovery that pharmaceutical compositions comprising small particles of an active pharmaceutical ingredient can be administered to the pilosebaceous unit. The pharmaceutical composition can comprise SHR0302 or spironolactone as an active pharmaceutical ingredient.

19 Claims, 14 Drawing Sheets

(56) References Cited

OTHER PUBLICATIONS

Leite-Silva et al. "The Influence of Emollients on Dermal and Transdermal Drug Delivery" in Percutaneous Penetration Ehancers Drug penetration Into/Through the Skin Methodology and General Considerations, May 4, 2017 (May 4, 2017), Springer-Verlag Berlin Heidelberg, XP055889873, pp. 77-93.
"Cyclomethicone/Dimethicone," Handbook of Pharmaceutical Excipients, Fifth Edition, Jan. 1, 2006 (Jan. 1, 2006), Pharmaceutical Press, XP055889869, 6 pages.
Wu Ke et al., "Quality Assessment of API in Semisolid Topical Drug Products," The Role of Microstructure in Topical Drug Product Development, Aug. 7, 2019 (Aug. 7, 2019), Springer International Publishing, XP055895570, p. 113.
Annika Vogt et al., "Follicular Targeting—A Promising Tool in Selective Dermatotherapy," JID Symposium Proceedings, (2005), 10(3):252-255.
D. W. Osborne et al., "The Influence of Skin Surface Lipids on Topical Formulations," Marcel Dekker, New York (1990), pp. 69-86.
Andrea C. Lauer et al., "Transfollicular Drug Delivery", Pharmaceutical Research, (1995), 12(2):179-186.
Amit Verma et al., "Transfollicular drug delivery: current perspectives," Research and Reports in Transdermal Drug Delivery, (2016), 5:1-17.
Attwa et al., "Efficacy and safety of topical spironolactone 5% gel versus placebo in the treatment of acne vulgaris," Egyptian J. Dermatol. Venerol., (2019), 39:89-94.
J.W. Charny et al., "Spironolactone for the treatment of acne in women, a retrospective study of 110 patients," Int. J. Womens Dermatol., (2017), 3(2): 111-115.

COMPOSITIONS AND METHODS FOR DEEP DERMAL DRUG DELIVERY

CROSS REFERENCE TO RELATED APPLICATIONS

This application is a continuation of U.S. Ser. No. 17/527,856, filed Nov. 16, 2021 and claims priority to U.S. Provisional Application No. 63/114,887 filed on Nov. 17, 2020 and U.S. Provisional Application No. 63/221,349 filed on Jul. 13, 2021, the disclosures of which are incorporated herein in their entirety by reference.

FIELD OF THE INVENTION

The subject matter disclosed herein generally relates to pharmaceutical compositions for the topical administration of a drug to the pilosebaceous unit and methods for administering the same. As disclosed herein, the inventors of the present invention have made the surprising discovery that pharmaceutical compositions comprising small particles of an active pharmaceutical ingredient can be targeted to the pilosebaceous unit. In preferred embodiments, the pharmaceutical composition comprises SHR0302 or spironolactone as an active pharmaceutical ingredient.

BACKGROUND OF THE INVENTION

Transdermal and topical delivery of drugs have a variety of advantages compared with other routes of administration. Transdermal and topical delivery can be used to deliver drugs continuously into the systemic circulation and circumvent first-pass metabolism. In contrast, there is a significant first-pass effect of the liver that can prematurely metabolize drugs for oral drug delivery. Transdermal and topical delivery also have advantages over intravenous administration, which must be sterile products and can be painful thereby increasing noncompliance by patients. Transdermal delivery on the other hand can be non-sterile, non-invasive and self-administered.

Traditional drug delivery systems have focused on administration via the transepidermal route of delivery. Andrea C. Lauer et al., Transfollicular Drug Delivery, Pharmaceutical Research 12:2 (1995). The skin consists primarily of four layers: (a) the stratum corneum (nonviable epidermis), (b) viable epidermis, (c) dermis, and (d) subcutaneous tissues. The skin also contains appendages in the form of terminal hairs, which may extend more than 3 mm below the skin surface into the subcutaneous fatty tissue and vellus hair, which is the fine, often unnoticed body hair that extends less than 1 mm into the dermis. The hair follicle, hair shaft, and sebaceous gland, which secrets a lubricating oil matter into the hair follicles, comprise what is known as a pilosebaceous unit. While the stratum corneum has traditionally been viewed as the primary pathway for the penetration of drugs, it is also the main barrier to percutaneous absorption. In the past, researchers have questioned the significance of the pilosebaceous unit in drug delivery.

More recently, however, the potential role of the pilosebaceous unit and alternative mechanisms for the transdermal delivery of drugs have been investigated. Amit Verma et al., Transfollicular drug delivery: current perspectives, Research and Reports in Transdermal Drug Delivery (Apr. 20, 2016). The mammalian hair follicle is a complex, dynamic structure in which unique biochemical and immunological reactions occur. While the pilosebaceous unit may be an acceptable target for drug delivery, there are several challenges to drug delivery to the pilosebaceous unit. One of the challenges relating to drug delivery to the pilosebaceous unit is the need to bypass the stratum corneum, which extends approximately 10-20 µm deep and the upper capillary plexus, which extends approximately 80 µm deep.

There is currently a need for pharmaceutical compositions capable of penetrating deeper into the dermis, approximately 1,000 µm to 2,000 µm to the pilosebaceous unit. There is an unmet need for novel pharmaceutical compositions and methods of administering drugs via the pilosebaceous unit.

SUMMARY OF THE INVENTION

The present invention relates to pharmaceutical compositions for the topical administration of a drug to the pilosebaceous unit and methods for administering the same. The inventors of the present invention have made the surprising discovery that a pharmaceutical composition comprising small particles of an active pharmaceutical ingredient can be delivered to the pilosebaceous unit resulting in deeper penetration into the dermis and improved efficacy. In preferred embodiments, the pharmaceutical composition comprises SHR0302 or spironolactone as an active pharmaceutical ingredient.

In certain embodiments of the present invention, a pharmaceutical composition is provided comprising a therapeutically effective amount of an active pharmaceutical ingredient and a silicone selected from the group consisting of dimethicone, cyclomethicone, and combinations thereof. The active pharmaceutical ingredient has a primary particle size distribution that is characterized by a D90 value of less than about 20 µm. In certain embodiments, the pharmaceutical ingredient has a primary particle size distribution that is characterized by a D90 value of less than about 10 µm or more preferably less than about 5 µm. In certain embodiments, the composition comprises about 0.10% w/w to about 7.5% w/w of the active pharmaceutical ingredient. The pharmaceutical compositions of the present invention can be capable of delivering the active pharmaceutical ingredient to the pilosebaceous unit. In certain embodiments, the active pharmaceutical ingredient is capable of achieving dermal penetration of at least 1 mm in the subject.

In certain embodiments of the present invention, a pharmaceutical composition is provided comprising a therapeutically effective amount of SHR0302 or a pharmaceutically acceptable salt thereof. The SHR0302 can have a primary particle size distribution characterized by a D90 value of less than about 20 µm, less than about 10 µm, or more preferably less than about 5 µm. The SHR0302 can further have a primary particle size distribution characterized by a D50 value of less than about 5 µm, less than about 1 µm, or more preferably less than about 0.7 µm. The SHR0302 can further have a primary particle size distribution characterized by a D10 value of less than about 1 µm, less than about 0.5 µm, or more preferably less than about 0.25 µm.

The pharmaceutical composition further comprises a silicone selected from the group consisting of dimethicone, cyclomethicone, and combinations thereof. In certain embodiments of the present invention, the pharmaceutical composition comprises SHR0302 suspended in at least one of dimethicone and cyclomethicone.

In certain embodiments, the pharmaceutical composition can comprise about 0.10% w/w to about 5% w/w of SHR0302 or a salt thereof. In preferred embodiments, the pharmaceutical composition can comprise from about 0.1% w/w to about 3% w/w of SHR0302 or a salt thereof.

In certain embodiments of the present invention, a method of treating alopecia areata in a subject in need thereof is provided. The method comprises topically administering to the subject the pharmaceutical compositions of SHR0302 described herein. In the methods of the present invention, the SHR0302 or salt thereof can be delivered to the pilosebaceous unit. In the methods disclosed herein, administration of the pharmaceutical composition can result in dermal penetration of SHR0302 of at least about 1 mm in the subject, and preferably to the depth of the hair bulb for a terminal hair, about 2 to 3 mm in the subject.

In certain embodiments of the present invention, a pharmaceutical composition is provided comprising a therapeutically effective amount of spironolactone or a pharmaceutically acceptable salt thereof. The spironolactone can have a primary particle size distribution characterized by a D90 value of less than about 6 μm, less than about 1 μm, or more preferably less than about 0.25 μm. The spironolactone can further have a primary particle size distribution characterized by a D50 value of less than about 2.7 μm, less than about 0.75 μm, or more preferably less than about 0.15 μm. The spironolactone can further have a primary particle size distribution characterized by a D10 value of less than about 1.2 μm, less than about 0.50 μm, or more preferably less than about 0.10 μm.

The pharmaceutical composition further comprises a silicone selected from the group consisting of dimethicone and cyclomethicone. In certain embodiments of the present invention, the pharmaceutical composition of spironolactone is an oil-in-water emulsion.

Further, the pharmaceutical composition can comprise about 0.10% w/w to about 7.5% w/w of spironolactone or a salt thereof. In certain embodiments, the pharmaceutical composition can comprise from about 0.5% w/w to about 5% w/w of spironolactone or a salt thereof.

In certain embodiments of the present invention, a pharmaceutical composition is provided comprising a therapeutically effective amount of spironolactone or a pharmaceutically acceptable salt thereof and water. The spironolactone can have a primary particle size distribution characterized by a D90 value of less than about 6 μm, less than about 1 μm, or more preferably less than about 0.25 μm. The spironolactone can further have a primary particle size distribution characterized by a D50 value of less than about 2.7 μm, less than about 0.75 μm, or more preferably less than about 0.15 μm. The spironolactone can further have a primary particle size distribution characterized by a D10 value of less than about 1.2 μm, less than about 0.50 μm, or more preferably less than about 0.10 μm.

In certain embodiments, the pharmaceutical composition comprises about 0.10% w/w to about 7.5% w/w of spironolactone or a salt thereof. In certain embodiments, the pharmaceutical composition can comprise from about 0.5% w/w to about 5% w/w of spironolactone or a salt thereof. In certain embodiments, the pharmaceutical composition is an aqueous suspension. In certain embodiments, the pharmaceutical composition further comprises dioctyl sodium sulfosuccinate and/or hydroxyl propyl cellulose. In certain embodiments, the pharmaceutical composition comprises about 0.01% w/w to about 1% w/w of dioctyl sodium sulfosuccinate and/or about 0.01% to about 1.5% w/w of hydroxyl propyl cellulose.

In certain embodiments of the present invention, a pharmaceutical composition is provided consisting essentially of or consisting of a therapeutically effective amount of spironolactone or a pharmaceutically acceptable salt thereof, dioctyl sodium sulfosuccinate, hydroxyl propyl cellulose, and water. The spironolactone can have a primary particle size distribution characterized by a D90 value of less than about 6 μm, less than about 1 μm, or more preferably less than about 0.25 μm. The spironolactone can further have a primary particle size distribution characterized by a D50 value of less than about 2.7 μm, less than about 0.75 μm, or more preferably less than about 0.15 μm. The spironolactone can further have a primary particle size distribution characterized by a D10 value of less than about 1.2 μm, less than about 0.50 μm, or more preferably less than about 0.10 μm.

In certain embodiments, the pharmaceutical composition comprises about 0.10% w/w to about 7.5% w/w of spironolactone or a salt thereof. In certain embodiments, the pharmaceutical composition can comprise from about 0.5% w/w to about 5% w/w of spironolactone or a salt thereof. In certain embodiments, the pharmaceutical composition is an aqueous suspension. In certain embodiments, the pharmaceutical composition comprises about 0.01% w/w to about 1% w/w of dioctyl sodium sulfosuccinate and about 0.01% to about 1.5% w/w of hydroxyl propyl cellulose.

In certain embodiments, the pharmaceutical composition is capable of delivering spironolactone to the pilosebaceous unit of a patient. In certain embodiments, the pharmaceutical composition is capable of achieving dermal penetration of at least 1 mm in the patient, and preferably about 2 or 3 mm in the subject.

In certain embodiments of the present invention, a method of treating acne in a subject in need thereof is provided. In certain embodiments, the subject is a human male or female. In preferred embodiments, the subject is a female human. The method comprises topically administering to the subject the pharmaceutical compositions of spironolactone described herein. In the methods of the present invention, the spironolactone or salt thereof can be delivered to the pilosebaceous unit. In the methods disclosed herein, administration of the pharmaceutical composition can result in dermal penetration of spironolactone of at least 1 mm in the subject, and preferably about 2 or 3 mm in the subject.

BRIEF DESCRIPTION OF THE DRAWINGS

The accompanying drawings, which are incorporated herein and form part of the disclosure, help illustrate various embodiments of the present invention and, together with the description, further serve to describe the invention to enable a person skilled in the pertinent art to make and use the embodiments disclosed herein.

DETAILED DESCRIPTION OF THE INVENTION

Figure 1:
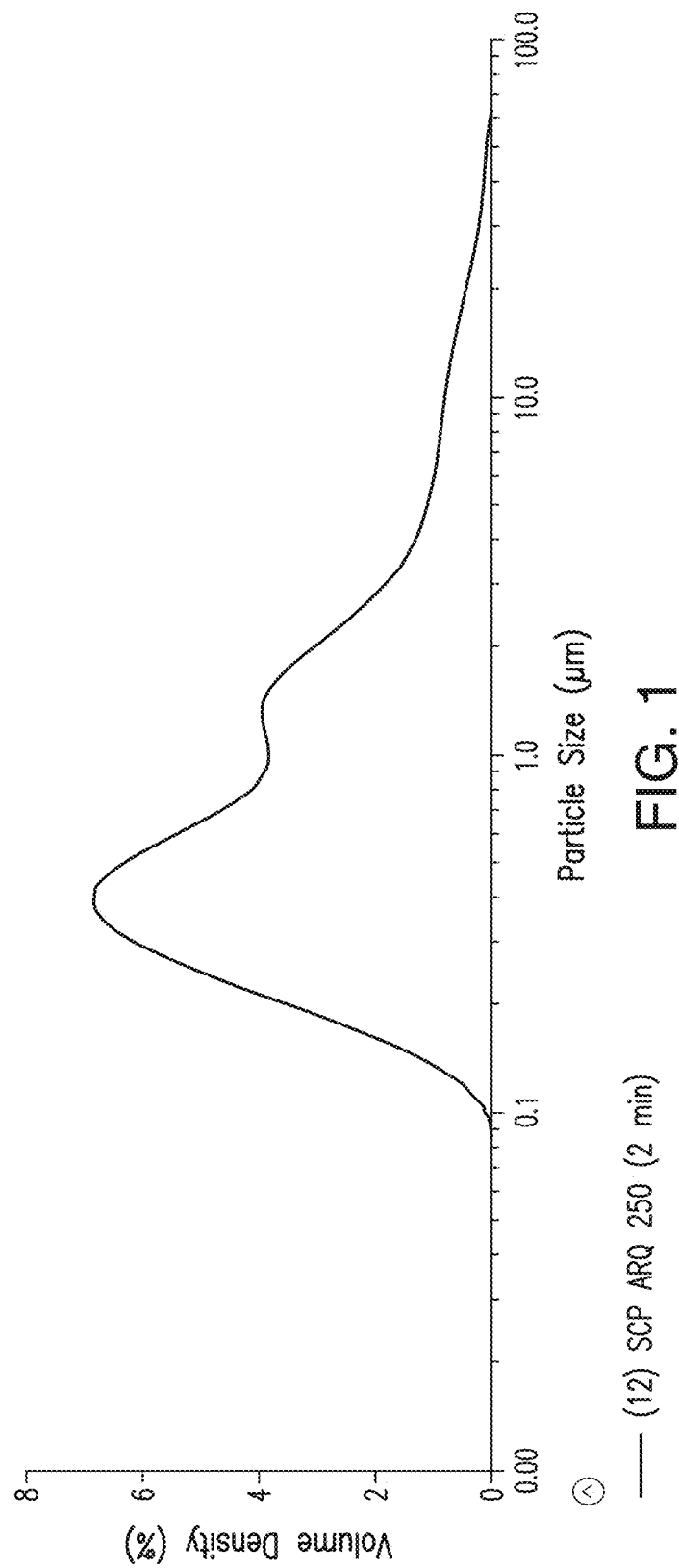
FIG. 1 shows a particle size distribution plot of SHR0302 in an exemplary pharmaceutical composition.

Before the present invention is described in detail below, it is to be understood that this invention is not limited to the particular methodology, protocols, and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art to which this invention belongs.

All publications, patents and patent applications cited herein are hereby incorporated by reference in their entirety unless otherwise stated. Where the same term is defined in a publication, patent, or patent application and the present disclosure incorporated herein by reference, the definition in the present disclosure represents a controlling definition. For publications, patents and patent applications referenced to describe a particular type of compound, chemistry, etc., the portion relating to such compounds, chemistry, etc. is the portion of the literature incorporated herein by reference.

Note that as used herein, the singular forms "a," "an," and "the" include plural referents unless the context clearly dictates otherwise. Thus, for example, "active ingredient" includes a single ingredient and two or more different ingredients and "sulfate salt" includes a single sulfate salt as well as two or more different sulfate salts.

The term "about" when used in connection with a numerical value is meant to encompass numerical values within a range having a lower limit that is 5% smaller than the indicated numerical value and having an upper limit that is 5% larger than the indicated numerical value.

The term "effective" refers to an amount of a compound, agent, substance, formulation or composition that is of sufficient quantity to result in a decrease in severity of disease symptoms, an increase in frequency and duration of disease symptom-free periods, or a prevention of impairment or disability due to the disease affliction. The amount may be as a single dose or according to a multiple dose regimen, alone or in combination with other compounds, agents or substances. One of ordinary skill in the art would be able to determine such amounts based on such factors as a subject's size, the severity of a subject's symptoms, and the particular composition or route of administration selected.

"Pharmaceutically acceptable" means generally safe for administration to humans or animals. Preferably, a pharmaceutically acceptable component is one that has been approved by a regulatory agency of the Federal or a state government or listed in the U.S. Pharmacopeia, published by the United States Pharmacopeial Convention, Inc., Rockville Md., or other generally recognized pharmacopeia for use in animals, and more particularly in humans.

A "pharmaceutical composition" according to the invention may be present in the form of a composition, wherein the different active ingredients and diluents and/or carriers are admixed with each other, or may take the form of a combined preparation, where the active ingredients are present in partially or totally distinct form. An example for such a combination or combined preparation is a kit-of-parts.

As used herein, the terms "subject" or "patient" most preferably refers to a human being. The terms "subject" or "patient" may include any mammal that may benefit from the compounds described herein.

A "therapeutic amount" or "therapeutically effective amount" is an amount of a therapeutic agent sufficient to achieve the intended purpose. The effective amount of a given therapeutic agent will vary with factors such as the nature of the agent, the route of administration, the size of the subject to receive the therapeutic agent, and the purpose of the administration. The effective amount in each individual case may be determined empirically by a skilled artisan according to established methods in the art.

The term "topical" with respect to administration of a drug or composition refers to the application of such drug or composition to the epithelial surface outside the body, including the skin or cornea. For this application, application to the inside of a body opening in which the mucosal surface does not contain pilosebaceous units, such as the mouth, vagina or rectum is not considered a topical application.

As used herein, "treat," "treating," or "treatment" of a disease or disorder means accomplishing one or more of the following: (a) reducing the severity and/or duration of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

The abbreviation "w/w" represents the relative concentration of the components in the composition as "weight to weight" (i.e., percentage refers to percentage of total weight), rather than based on volume or other quantities.

The present invention relates to pharmaceutical compositions for the topical administration of a drug to the pilosebaceous unit and methods for administering the same. The inventors of the present invention have made the surprising discovery that pharmaceutical compositions comprising small particles of an active pharmaceutical ingredient can be delivered to the pilosebaceous unit resulting in deeper penetration into the dermis and improved efficacy. In preferred embodiments, the pharmaceutical composition comprises SHR0302 or spironolactone as an active pharmaceutical ingredient.

In certain embodiments of the present invention, a pharmaceutical composition is provided comprising a therapeutically effective amount of an active pharmaceutical ingredient and a silicone selected from the group consisting of dimethicone, cyclomethicone, and combinations thereof. In certain embodiments, the amount of active pharmaceutical ingredient can range from about 0.01% w/w to about 10% w/w, or from about 0.01% w/w to about 7.5% w/w, or from about 0.01% w/w to about 5% w/w, or from about 0.1% w/w to about 3% w/w. Exemplary ranges are from about 0.1% w/w to about 10% w/w, or from about 0.1% w/w to about 7.5% w/w, or from about 0.1% w/w to about 5% w/w, or from about 0.1% w/w to about 5% w/w, or from about 1.0% w/w to about 5% w/w, or from about 0.3% w/w to about 5.0% w/w. For example, the pharmaceutical composition comprises any of the following w/w percents of active pharmaceutical ingredient: 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 7%, 1.8%, 1.9%, 1.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0% etc.

In the pharmaceutical compositions of the present invention, the active ingredient is present as small particles. Particle size of the drug can be assessed using laser diffraction methods. Laser diffraction is recognized by standards and guidance agencies including ISO and ASTM and is widely used to determine particle size distributions. In conducting the assessment, the sample is passed through a laser beam, which results in laser light scattered at a range of angles. Detectors placed at fixed angles measure the intensity of light scattered at that position. A mathematical model is then applied to generate a particle size distribution. The particle size values reported herein are determined by using a liquid or wet dispersion method.

In particle size determinations, the median value is defined as the value where half of the population resides above this point, and half resides below this point. For particle size distributions the median is called the D50. The D50 is the size that splits the distribution with half above and half below this diameter. The distribution width may also be characterized by citing one, two or three values on the x-axis, typically some combination of the D10, D50, and D90. The D50, the median, has been defined above as the diameter where half of the population lies below this value. Similarly, 90 percent of the distribution lies below the D90, and 10 percent of the population lies below the D10.

In certain embodiments, the active pharmaceutical ingredient has a primary particle size distribution that is characterized by a D90 value of less than about 20 µm, less than about 15 µm, less than about 10 µm, or more preferably less than about 5 µm. In certain embodiments, the active pharmaceutical ingredient has a primary particle size characterized by a D90 value of between about 0.001 µm, 0.01 µm, or 0.1 µm and about 5 µm, 10 µm, 15 µm, and 20. The active pharmaceutical ingredient can further have a primary particle size distribution characterized by a D50 value of less than about 5 µm, less than about 2 µm, less than about 1 µm, less than about 0.8 µm, or more preferably less than about 0.7 µm. In certain embodiments, the active pharmaceutical ingredient has a primary particle size characterized by a D50 value of between about 0.001 µm, 0.01 µm, or 0.1 µm and about 0.7 µm, 0.80 µm, 1.0 µm, 2.0 µm, or 5.0 µm. The active pharmaceutical ingredient can further have a primary particle size distribution characterized by a D10 value of less than about 1 µm, less than about 0.5 µm, less than about 0.4 µm, or more preferably less than about 0.25 µm. In certain embodiments, the active pharmaceutical ingredient has a primary particle size characterized by a D10 value of between about 0.0001 µm, 0.001 µm, or 0.01 µm and about 0.25 µm, 0.4 µm, 0.5 µm, or 1.0 µm.

In certain embodiments, the pharmaceutical compositions of the present invention are capable of delivering the active pharmaceutical ingredient to the pilosebaceous unit. In certain embodiments, active pharmaceutical ingredient is capable of achieving dermal penetration of at least 1 mm in the subject.

In certain embodiments of the present invention, the pharmaceutical composition comprises the JAK1 inhibitor, (3 aR,5 S,6aS)-N-(3-methoxyl-1,2,4-thiadiazol-5-yl)-5-(methyl(7H-pyrrolo[2,3-d]pyrimidin-4-yl)amino)hexahydrocyclopenta[c]pyrrole-2(1H)-carboxamide, which is also known as SHR0302 or ARQ-250. The terms SHR0302 and ARQ-250 are used interchangeably herein. The structure of SHR0302 is:

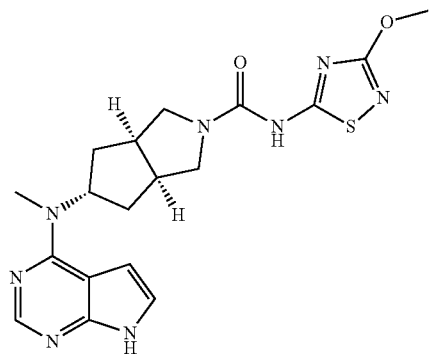 [SMILES: COc1nsc(NC(=O)N2C[C@H]3C[C@H](N(C)c4ncnc5[nH]ccc45)C[C@H]3C2)n1]

SHR0302 is a potent small molecule inhibitor of JAK1 that has been shown to have a high selectively for JAK1 over JAK2, and thus has the potential to treat inflammatory diseases without causing the hematopoietic adverse effects, such as anemia, thrombocytopenia, and neutropenia, associated with JAK2 inhibition. SHR0302 is disclosed in U.S. Pat. No. 9,527,851, which is hereby incorporated by reference.

In certain embodiments of the present invention, the pharmaceutical composition comprises the aldosternone agonist, 17-hydroxy-7α-mercapto-3-oxo-17α-pregn-4-ene-21-carboxylic acid γ-lactone acetate, which is also known as spironolactone. The structure of spironolactone is:

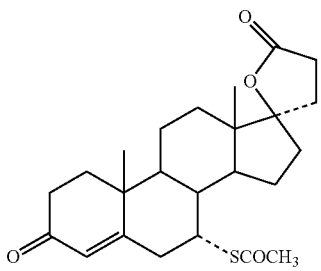

Spironolactone is a drug that acts at the mineralocorticoid receptor level by competitively inhibiting aldosterone binding. This steroidal compound has been used for blocking aldosterone-dependent sodium transport in the distal tubule of the kidney in order to reduce edema and to treat essential hypertension and primary hyperaldosteronism. Orally administrated spironolactone is also efficacious in the treatment of women with acne. E. M. Attwa et al., Efficacy and safety of topical spironolactone 5% gel versus placebo in the treatment of acne vulgaris, J. Dermatol. Venerol. 39:89-94 (2019); J. W. Charny et al., Spironolactone for the treatment of acne in women, a retrospective study of 110 patients, Int. J. Womens Dermatol. 3(2): 111-115 (2017). Spironolactone is commercially available under the tradenames ALDACTONE® and CAROSPIR®. Spironolactone is disclosed in U.S. Pat. No. 3,013,012, which is hereby incorporated by reference.

In the present invention, the pharmaceutical composition is administered topically. The pharmaceutical composition can include SHR0302 or spironolactone as a free base or a pharmaceutically acceptable salt. Suitable pharmaceutically acceptable salts can be found in Remington's Pharmaceutical Sciences, 17$^{th}$ ed., Mack Publishing Company (1985), which is incorporated by reference herein.

In certain embodiments, the pharmaceutical composition comprises SHR0302 having a primary particle size distribution characterized by a D90 value of less than about 20 μm, less than about 15 μm, less than about 10 μm, or more preferably less than about 5 μm. In certain embodiments, the SHR0302 has a primary particle size characterized by a D90 value of between about 0.01 μm, 0.1 μm, or 1.0 μm and about 5.0 μm, 10.0 μm, 15.0 μm, or 20.0 μm.

The SHR0302 can further have a primary particle size distribution characterized by a D50 value of less than about 5 μm, less than about 2 μm, less than about 1 μm, less than about 0.8 less, or more preferably less than about 0.7 μm. In certain embodiments, the SHR0302 has a primary particle size characterized by a D50 value of between about 0.001 μm, 0.01 μm, or 0.1 μm and about 0.7 μm, 0.8 μm, 1.0 μm, 2.0 μm, or 5.0 μm.

The SHR0302 can further have a primary particle size distribution characterized by a D10 value of less than about 1 μm, less than about 0.5 μm, less than about 0.4 μm, or more preferably less than about 0.25 μm. In certain embodiments, the SHR0302 has a primary particle size characterized by a D10 value of between about 0.0001 μm, 0.001 μm, or 0.01 μm and about 0.25 μm, 0.4 μm, 0.5 μm, or 1.0 μm.

In certain embodiments, the pharmaceutical composition comprises spironolactone having a primary particle size distribution characterized by a D90 value of less than about 6 μm, less than about 5 μm, less than about 2 μm, less than about 1 μm, less than about 0.5 μm, less than about 0.25 μm, or more preferably less than about 0.2 μm. In certain embodiments, the spironolactone has a primary particle size characterized by a D90 value of between about 0.001 μm, 0.01 μm, or 0.1 μm and about 0.2 μm, 0.25 μm, 0.5 μm, 1 μm, 2 μm, 5 μm, or 6 μm.

The spironolactone can further have a primary particle size distribution characterized by a D50 value of less than about 2.7 μm, less than about 2.0 μm, less than about 1.0 μm, less than about 0.75 μm, 0.5 μm, less than about 0.25 μm, less than about 0.2 μm, or more preferably less than about 0.15 μm. In certain embodiments, the spironolactone has a primary particle size characterized by a D50 value of between about 0.001 μm, 0.01 μm, or 0.1 μm and about 0.15 μm, 0.2 μm, 0.25 μm, 0.5 μm, 0.75 μm, 1.0 μm, 2.0 μm, or 2.7 μm.

The spironolactone can further have a primary particle size distribution characterized by a D10 value of less than about 1.2 μm, less than about 1.0 μm, less than about 0.5 μm, less than about 0.25 μm, less than about 0.15 μm, less than about 0.10 μm, or more preferably less than about 0.08 μm. In certain embodiments, the spironolactone has a primary particle size characterized by a D10 value of between about 0.0001 μm, 0.001 μm, or 0.01 μm and about 0.10 μm, 0.15 μm, 0.25 μm, 0.5 μm, 1.0 μm, or 1.2 μm.

In certain embodiments, the pharmaceutical compositions further comprise a silicone selected from the group consisting of dimethicone, cyclomethicone, or combinations thereof. Dimethicone, also known as polydimethylsiloxane (PDMS), is a polymeric organosilicon compound. Cyclomethicones are a group of methyl siloxanes, which unlike dimethicone, are cyclic organosilicon compounds. In certain embodiments, the pharmaceutical composition can comprise a combination of silicones, including dimethicone and cyclomethicone. For example, the pharmaceutical composition can comprise dimethicone-cyclomethicone-dimethicone/vinyl dimethicone. Additional methyl siloxane compatible excipients such as cyclopentasiloxane, dimethiconol and phenyl trimethicone may be added to dimethicone and/or cyclomethicone, to adjust aesthetics or viscosity. The silicone, such as dimethicone or cyclomethicone has a polarity similar to sebum, allowing for the pharmaceutical compositions to target follicular delivery.

In certain embodiments, the pharmaceutical composition is a suspension, wherein the active ingredient (e.g., SHR0302 or spironolactone) is suspended in the silicone (e.g., dimethicone or cyclomethicone). In certain embodiments, the pharmaceutical compositions can be formulated as an emulsion. For example, the pharmaceutical composition can be formulated as one of the following forms:

An oil-in-water emulsion: The product may be an emulsion comprising a discrete phase of a hydrophobic component and a continuous aqueous phase that includes water and optionally one or more polar hydrophilic excipients as well as solvents, co-solvents, salts, surfactants, emulsifiers, and other components. These emulsions may include water-soluble or water-swellable polymers that help to stabilize the emulsion.

A water-in-oil emulsion: The compositions may be an emulsion that includes a continuous phase of a hydrophobic component and an aqueous phase that includes water and optionally one or more polar hydrophilic carrier(s) as well as salts or other components. These emulsions may include oil-soluble or oil-swellable polymers as well as one or more emulsifier(s) to help to stabilize the emulsion.

A microemulsion: These are clear, thermodynamically stable isotropic liquid systems that contain oil, water and surfactants, frequently in combination with a cosurfactant. Microemulsions may be water continuous, oil continuous or bicontinuous mixtures. The formulations may optionally also contain water up to 60% by weight. Higher levels may be suitable in some compositions.

A nanoemulsion: These are isotropic dispersed systems that contain water, oil, and an emulsifier. The system may be an oily system dispersed in an aqueous system, or an aqueous system dispersed in an oily system forming droplets or oily phases of nanometric sizes. Nanoemulsions often have higher loading capacity for lipophilic active ingredients than microemulsions. Hydrophobic and hydrophilic active ingredients can also be formulated in nanoemulsion. Nanoemulsions may be formed by any suitable method known in the art, including high-pressure homogenization, microfluidization, and phase-inversion temperature.

In certain embodiments, the pharmaceutical composition consists essentially of the active ingredient and a silicone selected from the group consisting of dimethicone, cyclomethicone, or combinations thereof. Alternatively, the pharmaceutical compositions may be formulated with additional components, including conventionally found in cosmetic and pharmaceutical topical products.

In certain embodiments, the pharmaceutical composition is an suspension, wherein the active ingredient (e.g., spironolactone) is suspended in water. In certain embodiments, the pharmaceutical composition comprises between about 90% and 99% w/w water. In certain embodiments, the pharmaceutical composition consists essentially of or consists of spironolactone, dioctyl sodium sulfosuccinate, hydroxyl propyl cellulose, and water. In certain embodiments, the pharmaceutical composition does not comprise an additional thickening agent or a preservative. The inclusion of additional pharmaceutical excipients, such as an additional thickening agent or a preservative, can inactivate the ability of the suspended spironolactone to target the pilosebaceous unit.

In certain embodiments, the pharmaceutical composition may be formulated with additional components, including conventionally found in cosmetic and pharmaceutical topical products. In certain embodiments, the additional components comprise no more than 3%, 2%, 1%, or 0.5% w/w of the pharmaceutical composition. In certain embodiments, the pharmaceutical composition further comprises dioctyl sodium sulfosuccinate. In certain embodiments, the pharmaceutical composition further comprises hydroxyl propyl cellulose. In certain embodiments, the pharmaceutical composition comprises about 0.01% w/w to about 1% w/w of dioctyl sodium sulfosuccinate and/or about 0.01% to about 1.5% w/w of hydroxyl propyl cellulose.

In certain embodiments, the pharmaceutical composition further comprises one or more of hydroxypropylmethyl cellulose (HPMC), Polyvinylpyrrolidone (PVP K30), poloxamers such as Poloxamer 407, or polysorbates such as polysorbate 80. In certain embodiments, the pharmaceutical composition comprises about 0.1% to about 1.5% HPMC. In certain embodiments, the pharmaceutical composition comprises about 0.1% to about 1.5% PVP K30. In certain embodiments, the pharmaceutical composition comprises about 0.1% to about 1.5% Poloxamer 407. In certain embodiments, the pharmaceutical composition comprises about 0.1% to about 1.5% Polysorbate 80. In certain embodiments, the pharmaceutical composition comprises a pharmaceutically acceptable cellulose polymer such as methyl cellulose (MC), ethyl cellulose (EC), hydroxyethyl cellulose (HEC), carboxymethyl cellulose (CMC), sodium carboxymethyl cellulose (NaCMC), or microcrystalline cellulose. In certain embodiments, the pharmaceutical composition comprises about 0.1% to about 1.5% of a cellulose polymer.

Surfactants

In certain embodiments, the pharmaceutical composition may include one or more surfactants or co-surfactants. Surfactants include, but are not limited to short-chain alcohols, alkane diols and triols, alkyl phosphate esters, polyethylene glycols and glycol ethers, polyethylene stearyl ethers, including those sold under the tradenames Brij S2, Brij S20, Brij 721, Brij 38, Brij 52, Brij 56, and Brij W1, pyrrolidine derivatives, bile salts, sorbitan fatty acid esters and polyoxyethylene sorbitan fatty acid esters. In preferred embodiments, the surfactant is dioctyl sodium sulfosuccinate.

Polymers and Thickeners

In certain embodiments, the pharmaceutical composition may include insoluble organic polymeric thickeners such as natural and synthetic polymers or inorganic thickeners such as acrylates copolymer, carbomer 1382, carbomer copolymer type B, carbomer homopolymer type A, carbomer homopolymer type B, carbomer homopolymer type C, acrylamide/sodium acryloyldimethyl taurate copolymer, carboxy vinyl copolymer, carboxymethylcellulose, carboxypolymethylene, carrageenan, guar gum, xanthan gum, hydroxyethyl cellulose, hydroxypropyl cellulose, microcrystalline wax, and methylcellulose.

Additional Components

In certain embodiments, the pharmaceutical composition may include additional components such as carriers and excipients conventionally found in cosmetic and pharmaceutical topical products. Additional components including but not limited to antioxidants (e.g., BHT, BHA, ascorbic acid, tocopherol, citric acid, propyl gallate, sodium metabisulfite), sequestering agents, stabilizers, buffers, pH adjusting agents (preferably agents which result in an acidic pH, including but not limited to gluconolatone, citric acid, lactic acid, and alpha hydroxyacids), skin penetration enhancers, skin protectants (including but not limited to petrolatum, paraffin wax, dimethicone, glyceryl monoisostearate, isopropyl isostearate, isostearyl isostearate, cetyl alcohol, potassium cetyl phosphate, cetyl behenate and behenic acid), chelating agents, suspending agents (e.g., xanthan gum), dyes, pigments, diluents, fragrances, and other excipients to improve the stability or aesthetics, may be added to the composition.

Administration and Dosage

The present invention includes methods of treating hair loss conditions, such as alopecia, androgenic hair loss, hypothrichosis, and telogen effluvium. The methods can include treating a hair loss condition in a patient in need thereof by administering to the patient the compositions of SHR0302 or sprinolactone described herein.

In preferred embodiments, the present invention includes methods of treating alopecia areata (AA). AA is one of the most highly prevalent autoimmune diseases, leading to hair loss due to the collapse of immune privilege of the hair follicle and subsequent autoimmune destruction. AA is a skin disease that leads to hair loss on the scalp and elsewhere. Prior to the present invention, topical administration of JAK inhibitors have not shown reproducible clinical efficacy. Without being bound by theory, the inability of JAK inhibitors to treat AA prior to the claimed invention is believed to be due to insufficient drug delivery to the pilosebaceous unit, and more specifically, the hair bulb. The inventors of the present invention have made the surprising discovery that the pharmaceutical compositions disclosed herein are capable of penetrating the at least about 1 mm, at least about 2 mm, and at least about 3 mm into the hair follicle of an AA patient.

In certain embodiments, the present invention provides methods for treating AA in a patient in need thereof, comprising topically applying a therapeutically effective amount of the SHR0302 pharmaceutical compositions described herein to the patient. In certain embodiments, the active ingredient, SHR0302, can be administered in a therapeutically effective amount. In certain embodiments, the amount of SHR0302 can range from about 0.01% w/w to about 7.5% w/w, or from about 0.01% w/w to about 5% w/w, or from about 0.1% w/w to about 3% w/w. Exemplary ranges are from about 0.01% w/w to about 5% w/w, or from about 0.01% w/w to about 3% w/w, or from about 0.1% w/w to about 3% w/w, or from about 0.3% w/w to about 3.0% w/w. For example, the topical formulation comprises any of the following w/w percents of SHR0302: 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 7%, 1.8%, 1.9%, 1.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, etc.

The present invention further provides methods of treating acne in a patient in need thereof. Acne is a disorder of the pilosebaceous units located on the face, chest and back. The acne can be one selected from the group consisting of acne, acne vulgaris, inflammatory acne, non-inflammatory acne, acne fulminans, nodular papulopustular acne, acne conglobata, acne rosacea, rosacea, acne excoriee, adult-onset acne, persistent-recurrent acne past teenaged years, and acne associated with other disorders. In certain embodiments, the patient is a human male or female patient. In preferred embodiments, the patient is a human female. Further, the patient can be: (a) experiencing acne flares that cycle with menstruation; (b) inflicted with adult onset acne or persistent-recurrent acne past teenage years, even in the absence of clinical or laboratory signs of hyperandrogenism, (c) on oral contraceptives and exhibiting moderate to serve acne, especially with a hormonal pattern clinically; or (d) not responding to conventional therapy and who are not candidates for oral isotretinoin therapy.

In certain embodiments, the present invention provides methods for treating acne in a patient in need thereof, comprising topically applying a therapeutically effective amount of the spironolactone pharmaceutical compositions described herein to the patient. In certain embodiments, the active ingredient, spironolactone, can be administered in a therapeutically effective amount. In certain embodiments, the amount of spironolactone can range from about 0.01% w/w to about 10% w/w, or from about 0.01% w/w to about 7.5% w/w, or from about 0.01% w/w to about 5% w/w, or from about 0.1% w/w to about 3% w/w. Exemplary ranges are from about 0.1% w/w to about 10% w/w, or from about 0.1% w/w to about 7.5% w/w, or from about 0.1% w/w to about 5% w/w, or from about 0.1% w/w to about 3% w/w, or from about 1.0% w/w to about 5% w/w, or from about 0.3% w/w to about 5.0% w/w. For example, the topical formulation comprises any of the following w/w percents of spironolactone: 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 7%, 1.8%, 1.9%, 1.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, etc.

In certain embodiments, the pharmaceutical composition is administered topically as a regimen, such as at regular intervals. For example, a topical pharmaceutical composition can be administered once daily, twice daily, thrice daily, once per week, twice per week, three times per week, or four times per week. The pharmaceutical compositions can be administered for a prescribed period of time. For example, a topical pharmaceutical composition can be administered for a period of about two weeks to at least about six months, or until an improvement in skin condition or disease is visually observed. Exemplary periods of time for the treatment regimen include two weeks, one month, six weeks, two months, three months, four months, five months, six months, seven months, eight months, nine months, or one year. In preferred embodiments, the topical pharmaceutical composition is administered twice or thrice daily for a period of at least 3 months, 4 months, 5 months, or 6 months.

The following examples illustrate certain embodiments of the invention without limitation.

EXAMPLES

While various embodiments have been described above, it should be understood that they have been presented by way of example only, and not limitation. Thus, the breadth and scope of the present disclosure should not be limited by any of the above-described exemplary embodiments. Moreover, any combination of the above-described elements in all possible variations thereof is encompassed by the disclosure unless otherwise indicated herein or otherwise clearly contradicted by context.

Comparative Example 1

Comparative Example 1 was prepared as a 0.3% SHR0302 topical cream having the composition set forth in Table 1.

TABLE 1

Composition of SHR0302 Cream

| Ingredient | SHR0302 0.3% Cream |
|---|---|
| SHR0302 | 0.30% w/w |
| Dimethyl Sulfoxide (DMSO) | 30.0% w/w |
| Propylene Glycol | 15% w/w |
| Polyethylene Glycol 200 | 15% w/w |
| Cyclomethicone | 7.0% w/w |
| ST-Elastomer 10 | 2.0% w/w |
| Dimethicone | 1.0% w/w |
| Pemulen TR 1 | 0.8% w/w |
| Carbopol 974P | 1.5% w/w |
| EDTA | 0.05% w/w |
| BHT | 0.05% w/w |
| Benzyl Alcohol | 2.0% w/w |
| D-Limonene | 0.1% w/w |
| Trolamine (25% solution to adjust pH) | q.s. ad pH 5.5 |
| Purified Water | q.s. ad 100% |
| Total | 100% |

Example 1

A pharmaceutical composition comprising 3% SHR0302 suspended in dimethicone was prepared. The SHR0302 used in the composition had a particle size distribution as set forth in FIG. 1. The primary particle size distribution of the SHR0302 is characterized by a D10 value of less than about 0.25 µm; a D50 value of less than about 0.7 µm; and a D90 value of less than about 5 µm. The pharmaceutical composition was a transparent solution due to the particles being too small to scatter visible light. A Malvern Metasizer Model 3000 using the Hydro MV dispersion unit was used to determine the particle size distribution profile of SHR0302. The sample preparation procedure performed was as follows: weigh 10-20 mg of SCP processed ARQ-250 into a 30-mL vial, add 20 mL of ethyl acetate, sonicate the suspension with an ultrasonic probe at 40% power for 2 minutes in a 5° C. water bath, and transfer the sample suspension to the Malvern Hydro MV dispersion unit to obtain obscuration between 5 and 15%. The instrument parameters were: (i) Refractive Index of Particles: 1.5; (ii) Refractive Index of Dispersant 1.395; (iii) Absorption Index: 0.01; (iv) Measurement Duration: 10 seconds; (v) Number of Measurements: 3; (vi) Stir Speed: 3500 rpm; (vii) Ultrasonics: Off.

Example 2

The ability of Comparative Example 1 and Example 1 to penetrate into human cadaver scalp skin was assessed. Two different human cadaver scalp skins (Donor A and B) were mounted on special tension cell. A dose (7.5 µL) of either Comparative Example 1 or Example 1 was applied to the scalp skin specimen for 6 hours. All formulation residue was washed from the skin. An 8 mm punch biopsy was taken from the dermis side of the skin and flash frozen in liquid nitrogen. Serial 10 µm cryosections were taken, wherein an hematoxylin and eosin (H&E) stain was prepared for every other section, and adjacent sections were retained for analysis using Fourier Transform Ion Cyclotron Resonance—High Resolution—Matrix Assisted Laser Desorption/Ionization Mass Spectrometry (FTICR-HR-MALDI). The FTICR-HR-MALDI analysis was performed using a Bruker 7T FTICR-HR-MALDI MS system.

Figure 2:
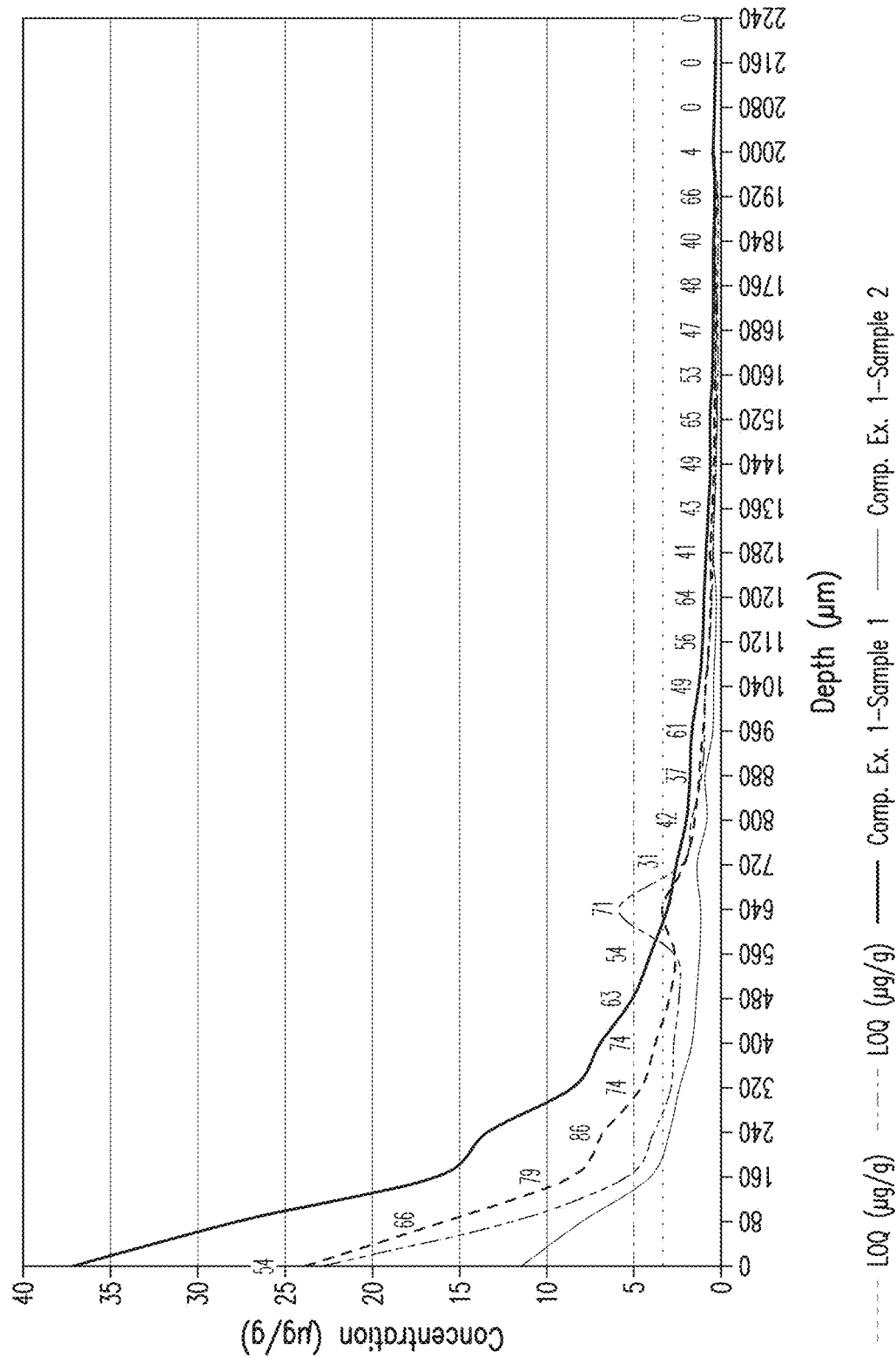
FIG. 2 shows a Fourier Transform Ion Cyclotron Resonance—High Resolution—Matrix Assisted Laser Desorption/Ionization Mass Spectrometry (FTICR-HR-MALDI) depth profile of an 0.3% SHR0302 topical 30% DMSO cream for a first donor (Donor A).
Figure 4:
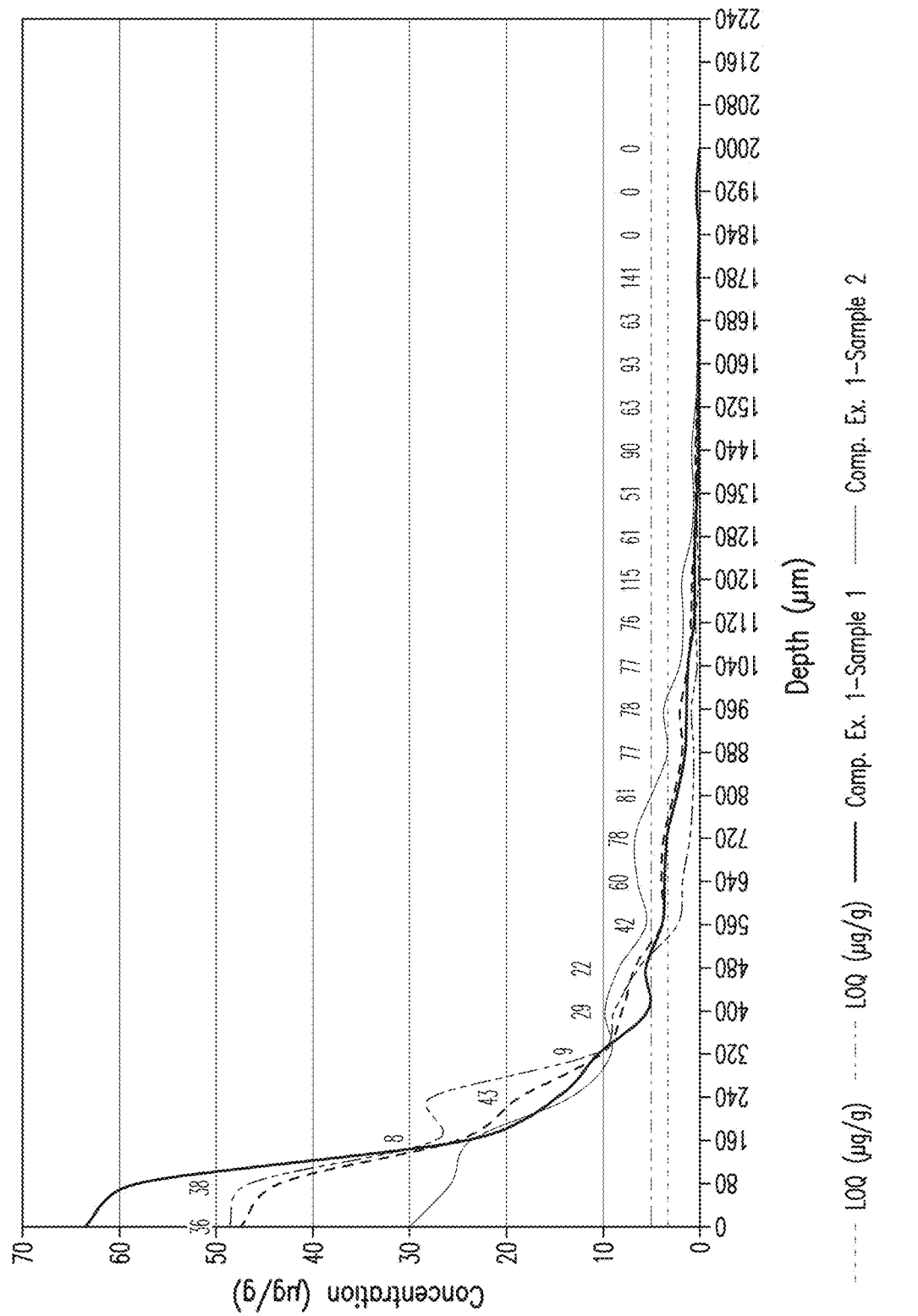
FIG. 4 shows a FTICR-HR-MALDI depth profile of an 0.3% SHR0302 topical 30% DMSO cream for a second donor (Donor B).

FIGS. 2 and 4 show a FTICR-HR-MALDI depth profile of an 0.3% SHR0302 topical 30% DMSO cream for Donor A and Donor B, respectively. As shown in FIG. 2, Comparative Example 1 achieved less than 160 µm of maximum dermal penetration in Donor A. As shown in FIG. 4, Comparative Example 1 achieved less than 500 µm of maximum dermal penetration in Donor B. The results are consistent with a pharmaceutical composition capable of delivering drug across the stratum corneum and indicate that drug is not penetrating below the upper capillary plexus.

Figure 3:
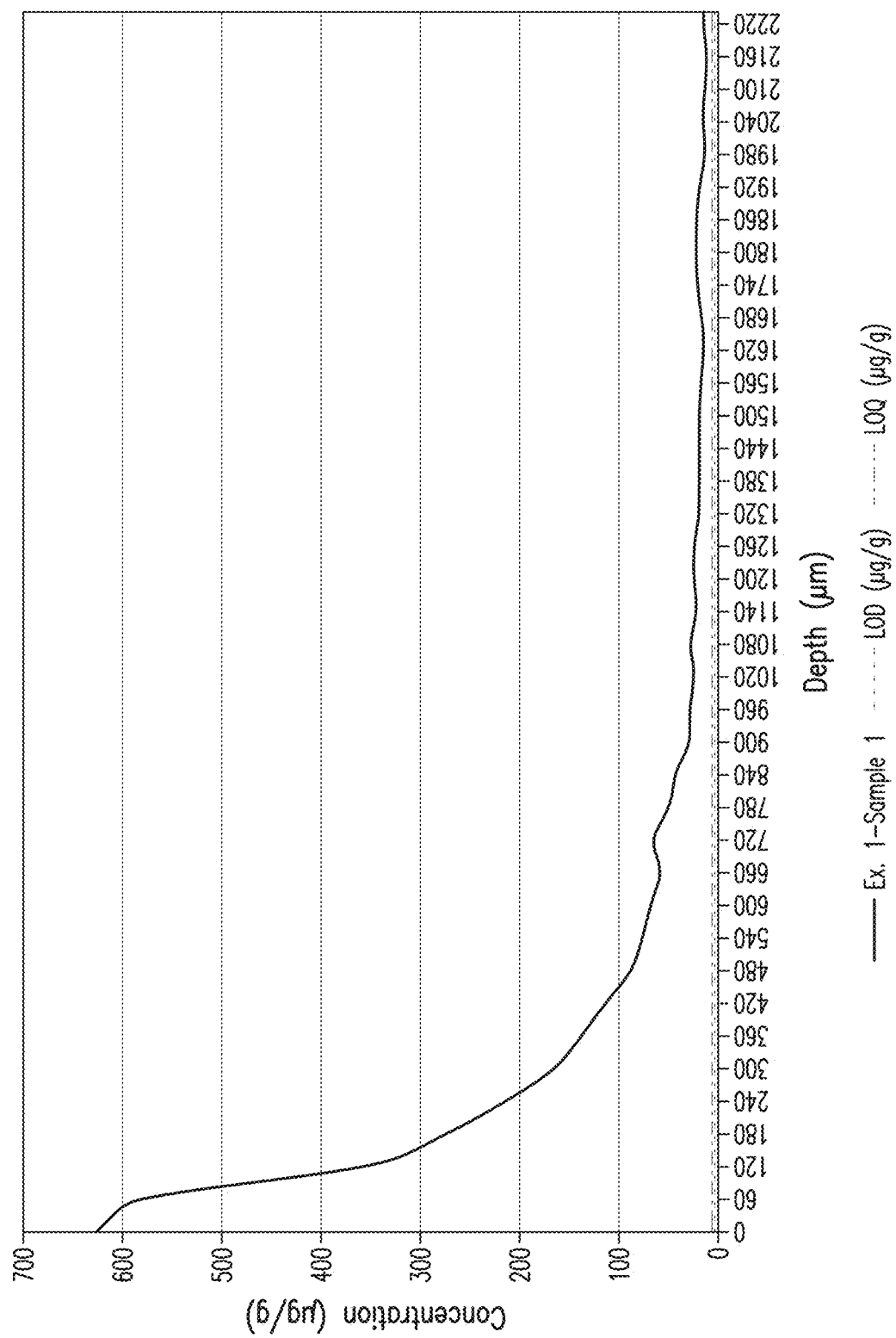
FIG. 3 shows a FTICR-HR-MALDI depth profile of a 3% SHR0302 topical suspension in dimethicone for a first donor (Donor A).
Figure 5:
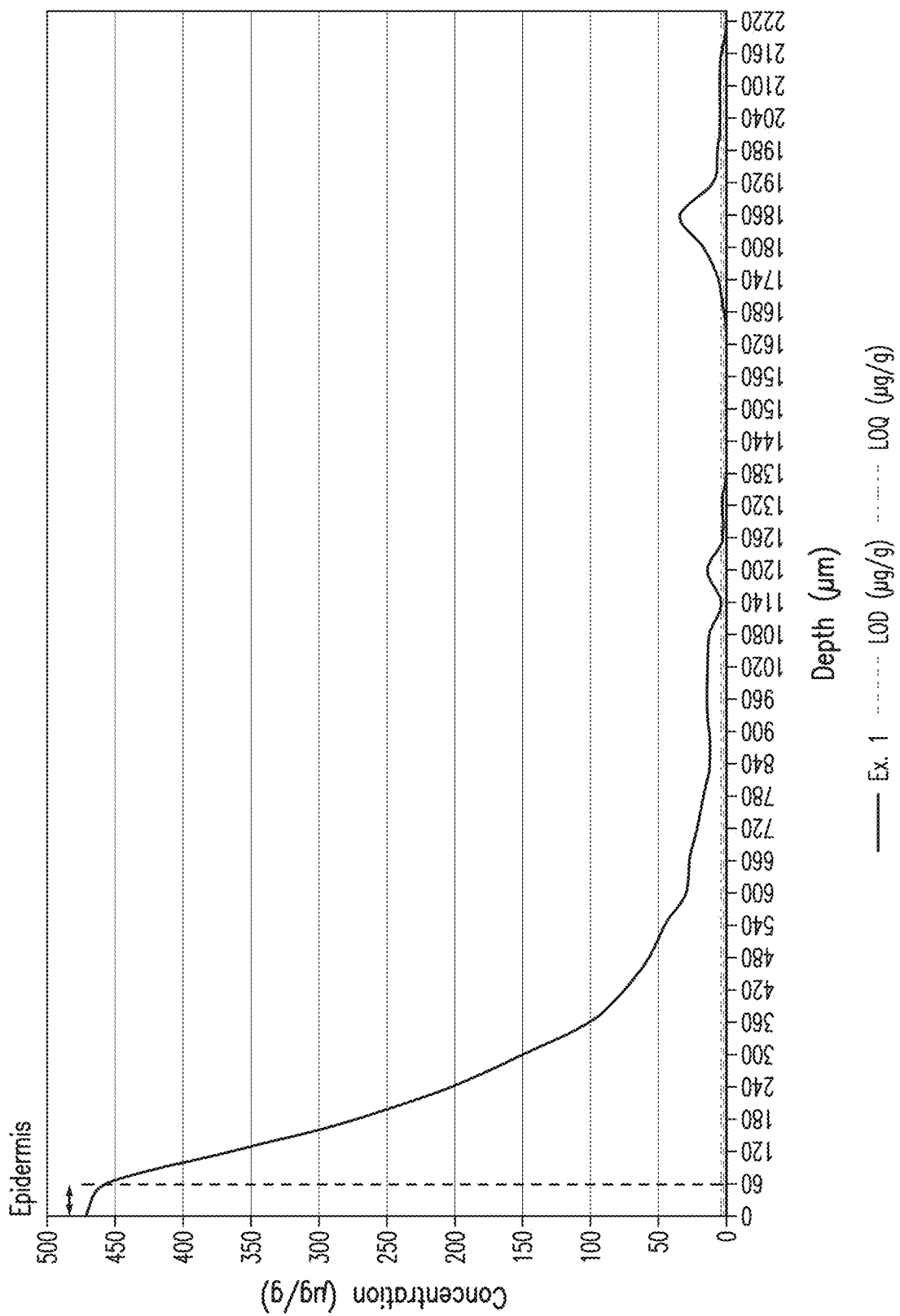
FIG. 5 shows a FTICR-HR-MALDI depth profile of a 3% SHR0302 topical suspension in dimethicone for a second donor (Donor B).

FIGS. 3 and 5 show a FTICR-HR-MALDI depth profile of a 3% SHR0302 topical suspension in dimethicone for Donor A for Donor A and Donor B, respectively. As shown in FIGS. 3 and 5, Example 1 achieved greater than 1 mm of maximum dermal penetration. The results surprisingly show that the pharmaceutical composition is capable of delivering drug to the hair bulb.

Example 3

A 50 mg/mL aqueous suspension of 5% spironolactone containing 0.5% dioctyl sodium sulfosuccinate and 1% hydroxyl propyl cellulose was successfully nano-milled to provide stable submicron particles of suspension of drug particles after storage for two weeks at 5° C. and ambient light. The spironolactone had a particle size distribution as set forth in FIG. 6. A Horiba Laser Scattering Particle Size Distribution Analyzer Model LA-950 was used to determine the volume based distribution profile of spironolactone. Circulation, agitation, and ultrasound were all turned off and the instrument was set to manual iteration mode.

A stable 0.3% spironolactone oil-in-water emulsion was prepared having the composition set forth in Table 2:

TABLE 2

Composition of Spironolactone Oil-in-Water Emulsion

| Ingredient | Spironolactone Oil-in-Water Emulsion |
|---|---|
| Spironolactone | 0.30% w/w |
| Cyclomethicone | 10.0% w/w |
| Methylparaben | 0.10% w/w |
| Propylbaraben | 0.01% w/w |
| Sepineo P600 | 4.0% w/w |
| Purified Water | q.s. ad 100% |
| Total | 100% |

Example 4

Figure 6:
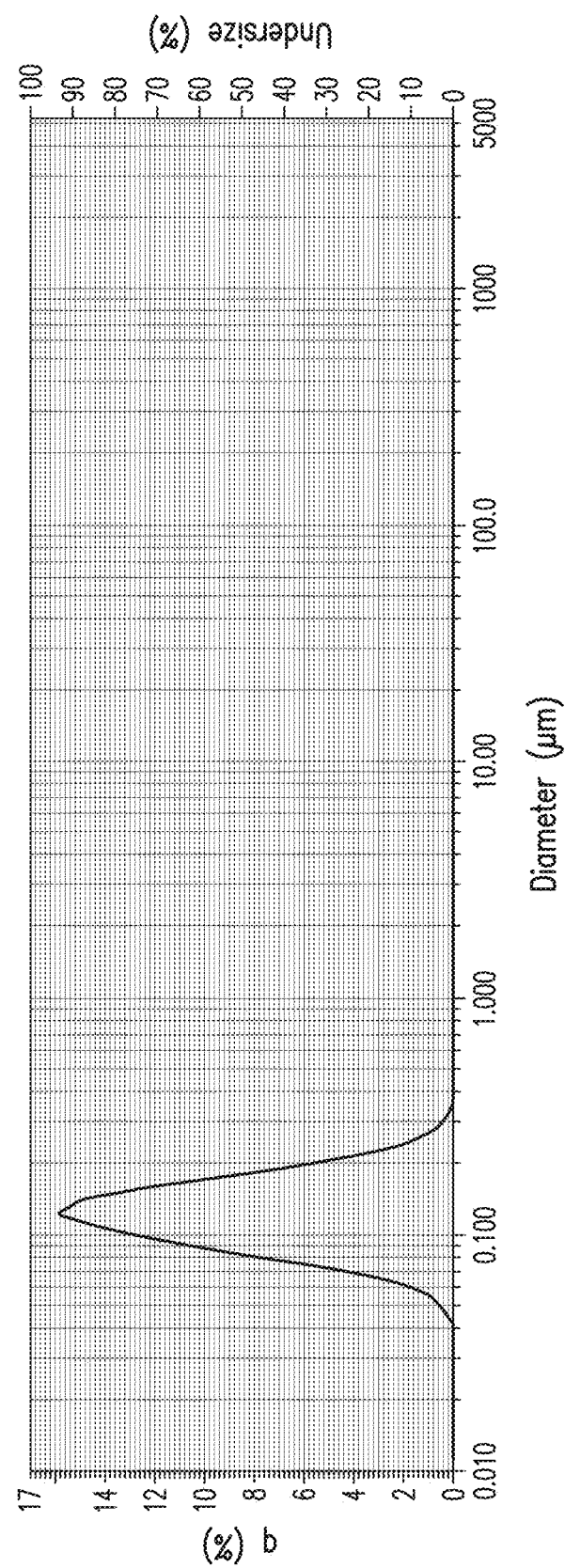
FIG. 6 shows a particle size distribution of spironolactone in a suspension of 5.0% spironolactone nano-milled in water with 0.05% dioctyl sulfosuccinate (DOSS) and 1.0% hydroxyl propyl cellulose.
Figure 7:
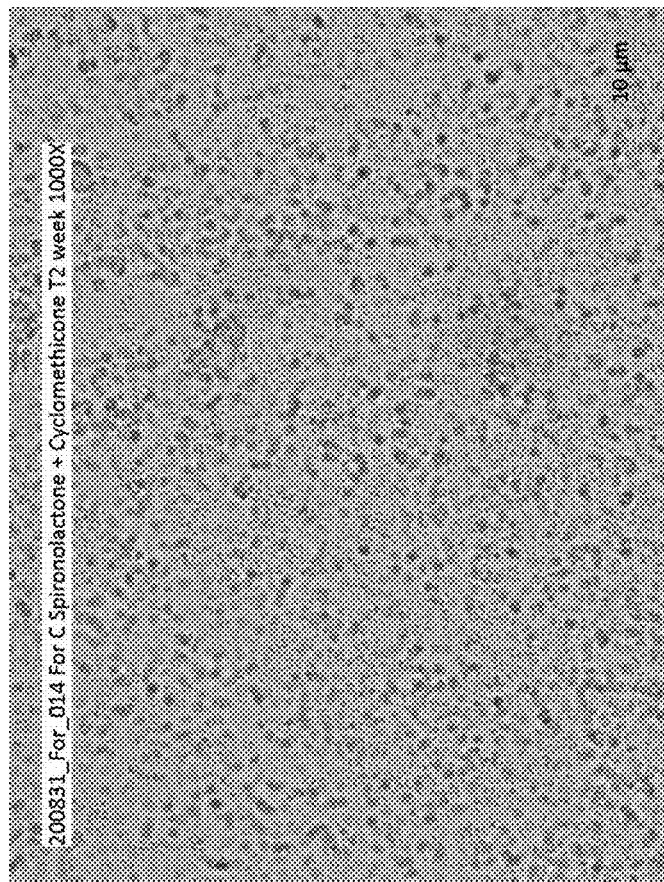
FIG. 7 is a micrograph taken two weeks after storage past completion of milling for a 5% spironolactone suspension in cyclomethicone that was roller milled to form a suspension having a D90 of less than about 5 μm.

A 5.0%-5.5% spironolactone suspension in water containing 0.05%-0.055% dioctyl sodium sulfosuccinate and 1.0-1.1% hydroxyl propyl cellulose was nano-milled to achieve the particle size distribution shown in FIG. 6. The composition of the finished product suspension is listed in Table 3 as Formulation 1. A 5% spironolactone suspension in cyclomethicone was roller milled to form a suspension having a D90 of less than about 5 µm as shown in FIG. 7 (microphotograph taken after two weeks of storage past completion of milling). The composition of this finished product suspension is listed in Table 3 as Formulation 2. A comparative gel formulation described in the literature was prepared and is listed in Table 3 as Comparative Gel. (Attwa EM, Ibrahim AM, Abd El-Halim MF, Mahmoud HM, Efficacy and safety of topical spironolactone 5% gel versus placebo in the treatment of acne vulgaris, Egypt J Dermatol Venerol (2019); 39:89-94.)

TABLE 3

Composition of Two Deep Dermal Drug Delivery Formulations and a Comparative Gel from the Literature.

| Ingredient | Formulation 1 (% w/w) | Formulation 2 (% w/w) | Comparative Gel (% w/w) |
|---|---|---|---|
| Spironolactone | 5.0-5.5 | 5.0 | 5.0 |
| Ethanol | — | — | 20.0 |
| Glycerin | — | — | 10.0 |
| Propylene glycol | — | — | 10.0 |
| Lactic acid | — | — | 5.0 |
| Methyl cellulose | — | — | 3.0 |
| Sodium benzoate | — | — | 0.03 |
| Cylclomethicone | — | 95.0 | — |
| Dioctyl sodium sulfo succinate | 0.05-0.055 | — | — |
| Hydroxyl propyl cellulose | 1.0-1.1 | — | — |
| Water | q.s. ad 100% | — | 46.97 |

In vitro skin penetration testing (IVPT) was used to determine how rapidly the different formulations crossed excised human skin. Human cadaver skin was procured from two donors (Caucasian female age=48 abdomen skin dermatomed to an average thickness of 580 µm and Hispanic male age=50 abdomen skin dermatomed to an average thickness of 910 µm). Dermatomed skin was received frozen from a US tissue bank and stored at −20° C. until use. Skin was loaded onto vertical Franz cells having a 0.503 cm² (8 mm in diameter) diffusion area and a receptor chamber filled with 3.0 ml of 4% BSA in water containing 0.01% gentamicin sulfate thermostated at 32° C. Using a positive displacement pipette, 5 microliters of each formulation was dosed on each Franz Cell (10 mg per square centimeter of skin). Receptor solutions were analyzed using a validated LC-MS/MS (Kinetex C18, 5 μm, 2.1×50 mm column, Shimadzu LC20ADXR pumps and AB Sciex API 4000 Turbo Spray detector). The cumulative amount of spironolactone assayed in the receptor solution is the average of four replicate IVPT measurements.

To determine the levels of spironolactone retained in the epidermis and dermis 24-hours after dosing the skin, the skin surface was cleaned of any unabsorbed and unpenetrated spironolactone. This was accomplished by wiping the tissue surface with a Q-tip wetted with 1×PBS three times followed by two tape strippings. The epidermis (including the stratum corneum) was removed from the dermis and soaked in 4.0 ml of a DMSO/Acetonitrile (ACN) (50/50 v/v) mixture for overnight at room temperature using an orbit shaker. The remaining dermis layer was cut into small pieces and extracted with 4.0 ml of the DMSO/ACN mixture for overnight at room temperature using an orbit shaker. Extracts of the dermis and epidermis were analyzed using a validated LC-MS/MS (Kinetex C18, 5 μm, 2.1×50 mm column, Shimadzu LC20ADXR pumps and AB Sciex API 4000 Turbo Spray detector).

Figure 8:
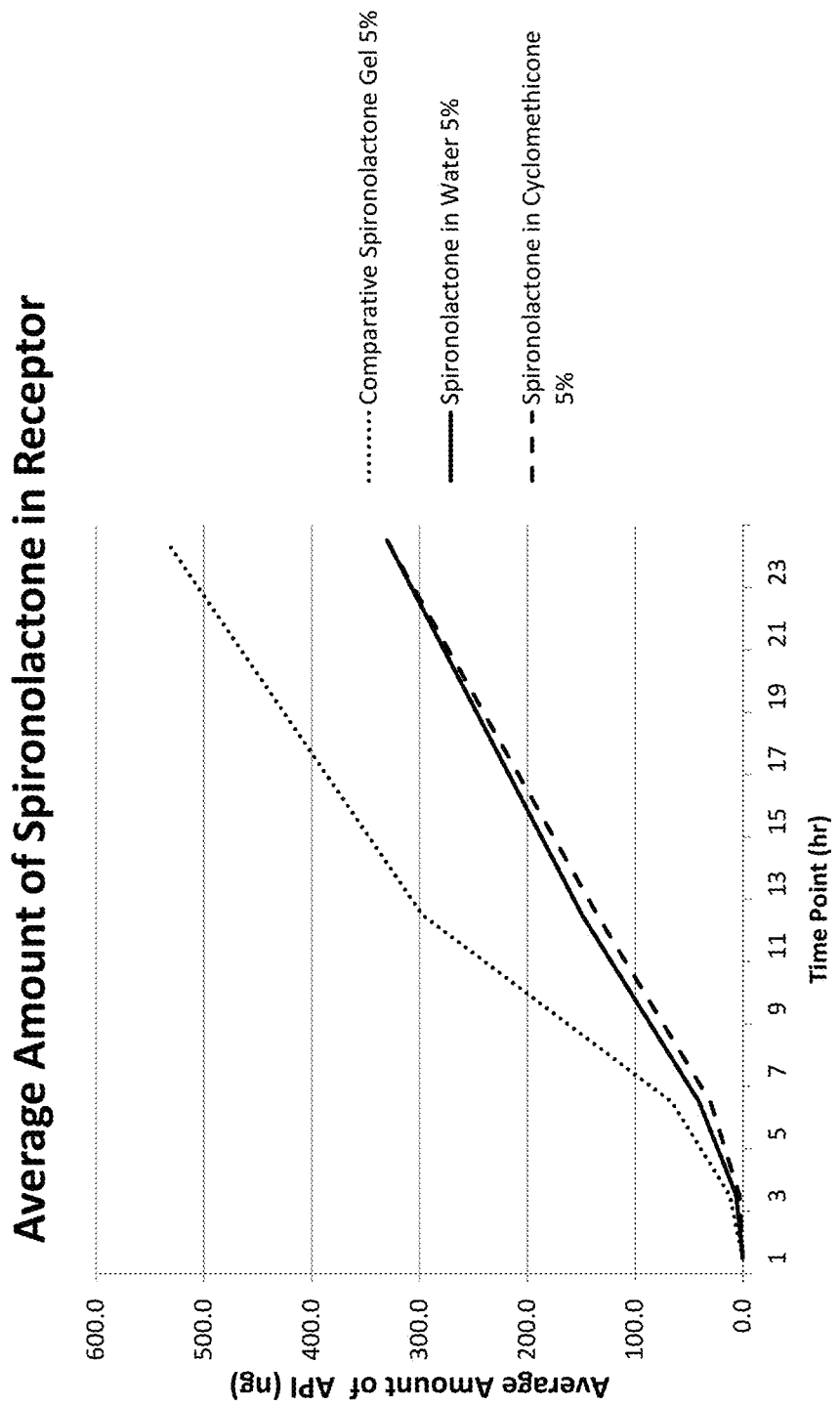
FIG. 8 shows the cumulative amount of spironolactone appearing in the receptor solution over 24 hours after a single 5.0 μl per cell (10 mg per cm$^2$ of skin tissue) for two exemplary formulations (Formulation 1 and Formulation 2, described in Example 4) and a Comparative Gel formulation (also described in Example 4).
Figure 9:
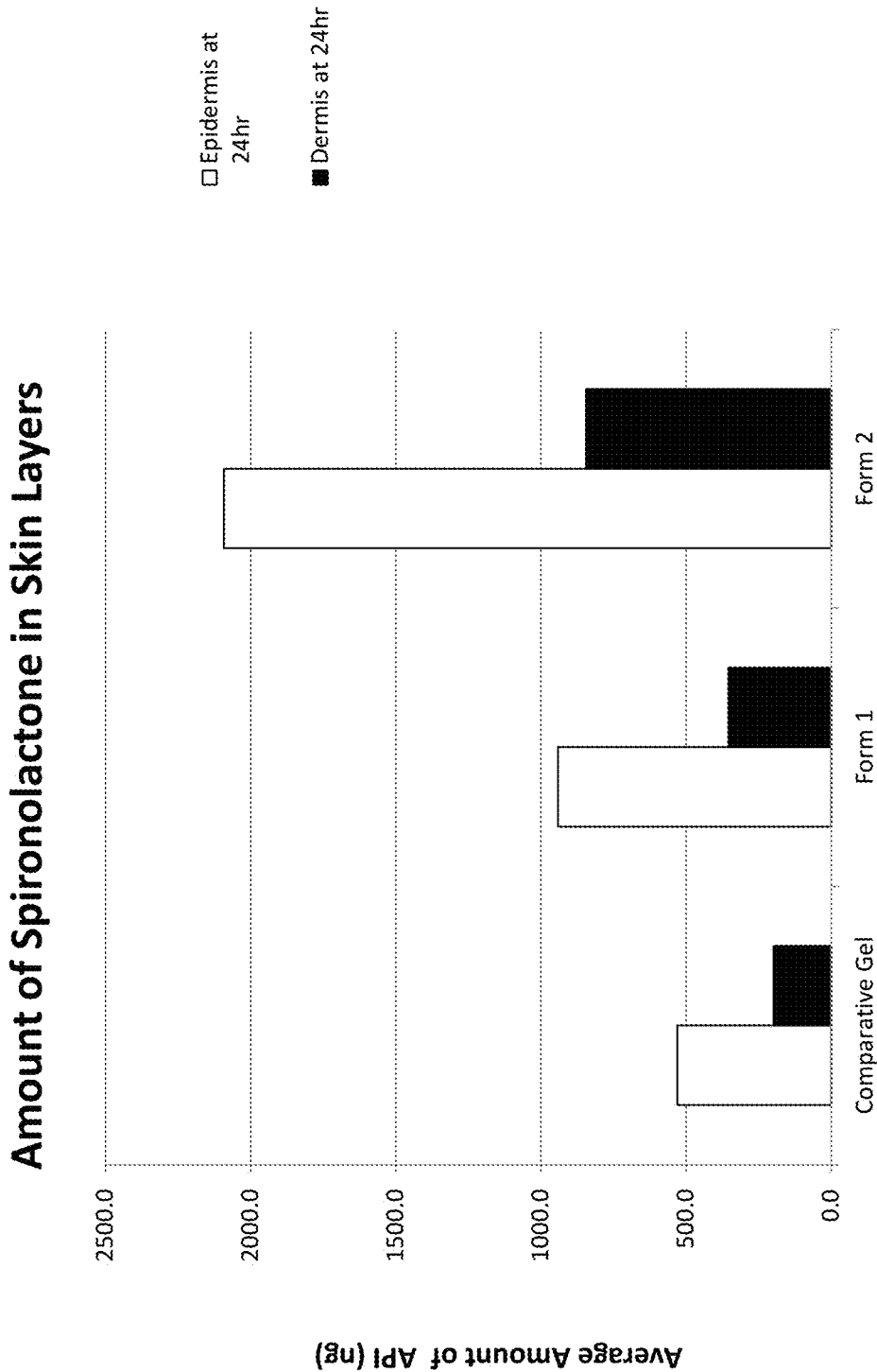
FIG. 9 shows the amount of spironolactone (ng) in the epidermis and dermis after 24 hours for two exemplary formulations (Formulation 1 and Formulation 2, described in Example 4) and a Comparative Gel formulation (also described in Example 4).

FIG. 8 illustrates the cumulative amount of spironolactone appearing in the receptor solution over 24 hours after a single 5.0 μl per cell (10 mg per cm² of skin tissue) for Formulation 1, Formulation 2, and the Comparative Gel. In FIG. 8, each plotted value is the average of four separate pieces of excised human skin. FIG. 9 illustrates the amount of spironolactone (ng) in the epidermis and dermis after 24 hours for Formulation 1, Formulation 2, and the Comparative Gel. As seen in FIG. 8 the comparative gel with 5% dissolved spironolactone delivered more spironolactone across excised human skin than either the 5% spironolactone water suspension or the 5% spironolactone cyclomethicone suspension. However, significantly greater deposition of spironolactone into the epidermis (location of the infundibulum of the pilosebaceous unit) for both suspensions is seen in FIG. 9. High levels of API in the epidermis and dermis indicates that spironolactone targets the pilosebaceous unit and has significantly greater follicular deposition from the aqueous suspension (D90<0.5 μm which is Formulation 1) and cyclomethicone suspension (D90<5.0 μm which is Formulation 2).

Example 5

Figure 10:
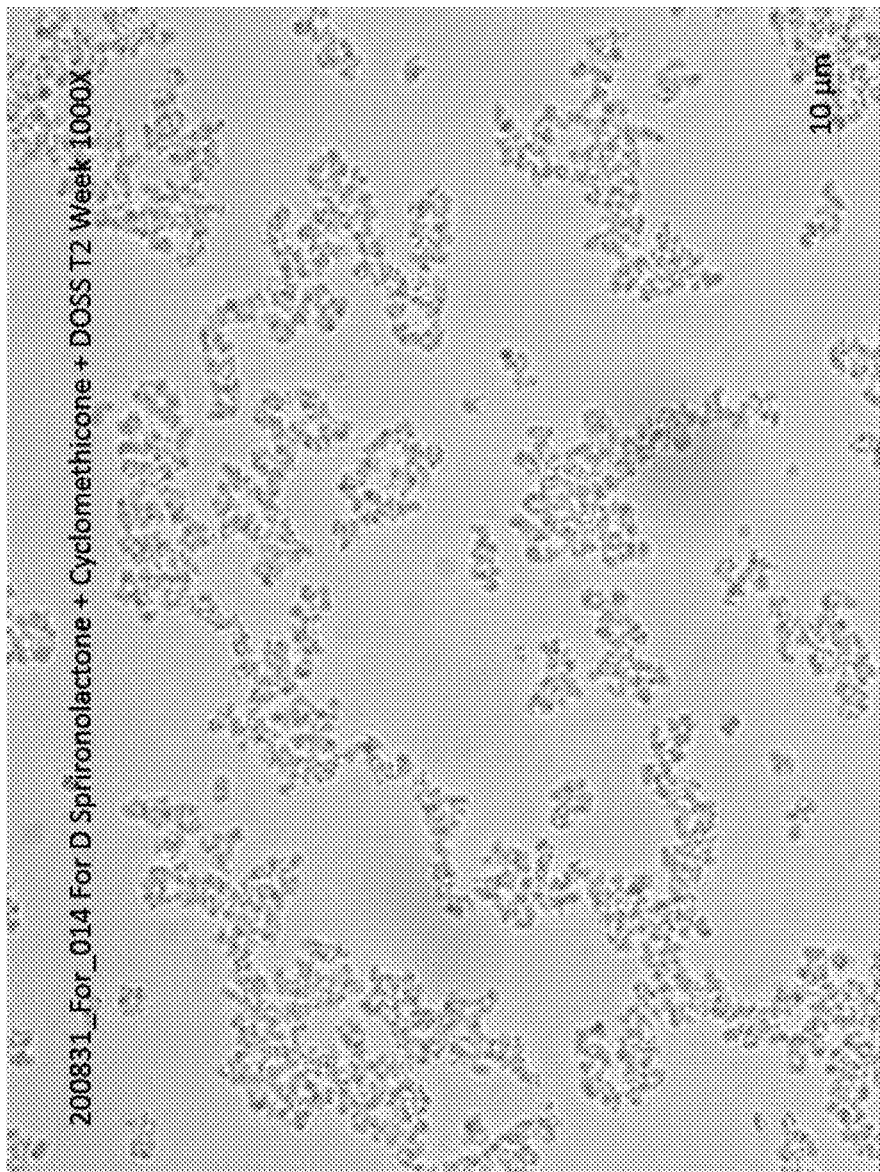
FIG. 10 is a micrograph taken two weeks after storage past completion of milling for a 5% spironolactone suspension in a 94.5:0.5 wt:wt blend of cyclomethicone and dioctyl sodium sulfosuccinate that was roller milled to form a suspension having a D90 of less than about 5 μm.

A 5.0%-5.5% spironolactone suspension in water containing 0.05%-0.055% dioctyl sodium sulfosuccinate and 1.0-1.1% hydroxyl propyl cellulose was nano-milled to achieve the particle size distribution shown in FIG. 6. The composition of the finished product suspension is listed in Table 1 as Formulation 1. An emulsion was formed by mixing the excipients disclosed in Table 1 as Emulsion 1. SEPINEO™ P 600 is a thickening, emulsifying and stabilizing polymer Acrylamide/Sodium Acryloyldimethyl Taurate Copolymer/Isohexadecane & Polysorbate 80 distributed by Seppic Inc., Fairfield N.J. Table 4 lists the final composition of Emulsion 1 in which the cyclomethicone oil phase was a 5% spironolactone suspension in cyclomethicone was roller milled to form a suspension having a D90 of less than about 5 μm as shown in FIG. 7 (microphotograph taken after two weeks of storage past completion of milling). Table 4 also lists the final composition of Emulsion 2 in which the cyclomethicone oil phase was 5% spironolactone suspension in a 94.5:0.5 wt:wt blend of cyclomethicone and dioctyl sodium sulfosuccinate that was roller milled to form a suspension having a D90 of less than about 5 μm as shown in FIG. 10 (microphotograph taken after two weeks of storage past completion of milling). A comparative gel formulation described in the literature was prepared and is listed in Table 4 as Comparative Gel. (Attwa EM, Ibrahim AM, Abd El-Halim MF, Mahmoud HM, Efficacy and safety of topical spironolactone 5% gel versus placebo in the treatment of acne vulgaris, Egypt J Dermatol Venerol (2019); 39:89-94.)

TABLE 4

Composition of Deep Dermal Drug Delivery Formulations and a Comparative Gel from the Literature.

| Ingredient | Formulation 1 (% w/w) | Emulsion 1 (% w/w) | Emulsion 2 (% w/w) | Comparative Gel (% w/w) |
|---|---|---|---|---|
| Spironolactone | 5.0-5.5 | 4.8 | 4.8 | 5.0 |
| Ethanol | — | — | — | 20.0 |
| Glycerin | — | — | — | 10.0 |
| Propylene glycol | — | — | — | 10.0 |
| Lactic acid | — | — | — | 5.0 |
| Methyl cellulose | — | — | — | 3.0 |
| Sodium benzoate | — | — | — | 0.03 |
| Cylclomethicone | — | 9.5 | 9.45 | — |
| Dioctyl sodium sulfosuccinate | 0.05-0.055 | 0.043 | 0.048 | — |
| Hydroxyl propyl cellulose | 1.0-1.1 | 0.86 | 0.86 | — |
| Sepineo P600 | — | 4.0 | 4.0 | — |
| Water | q.s. ad 100% | q.s. ad 100% | q.s. ad 100% | 46.97 |

In vitro skin penetration testing (IVPT) was used to determine how rapidly the different formulations crossed excised human skin. Human cadaver skin was procured from two donors (Caucasian female age=48 abdomen skin dermatomed to an average thickness of 580 μm and Hispanic male age=50 abdomen skin dermatomed to an average thickness of 910 μm). Dermatomed skin was received frozen from a US tissue bank and stored at −20° C. until use. Skin was loaded onto vertical Franz cells having a 0.503 cm² (8 mm in diameter) diffusion area and a receptor chamber filled with 3.0 ml of 4% BSA in water containing 0.01% gentamicin sulfate thermostated at 32° C. Using a positive displacement pipette, 5 microliters of each formulation was dosed on each Franz Cell (10 mg per square centimeter of skin). Receptor solutions were analyzed using a validated LC-MS/MS (Kinetex C18, 5 μm, 2.1×50 mm column, Shimadzu LC20ADXR pumps and AB Sciex API 4000 Turbo Spray detector). The cumulative amount of spironolactone assayed in the receptor solution is the average of four replicate IVPT measurements.

To determine the levels of spironolactone retained in the epidermis and dermis 24-hours after dosing the skin, the skin surface was cleaned of any unabsorbed and unpenetrated spironolactone. This was accomplished by wiping the tissue surface with a Q-tip wetted with 1×PBS three times followed by two tape strippings. The epidermis (including the stratum corneum) was removed from the dermis and soaked in 4.0 ml of a DMSO/Acetonitrile (ACN) (50/50 v/v)

mixture for overnight at room temperature using an orbit shaker. The remaining dermis layer was cut into small pieces and extracted with 4.0 ml of the DMSO/ACN mixture for overnight at room temperature using an orbit shaker. Extracts of the dermis and epidermis were analyzed using a validated LC-MS/MS (Kinetex C18, 5 μm, 2.1×50 mm column, Shimadzu LC20ADXR pumps and AB Sciex API 4000 Turbo Spray detector).

Figure 11:
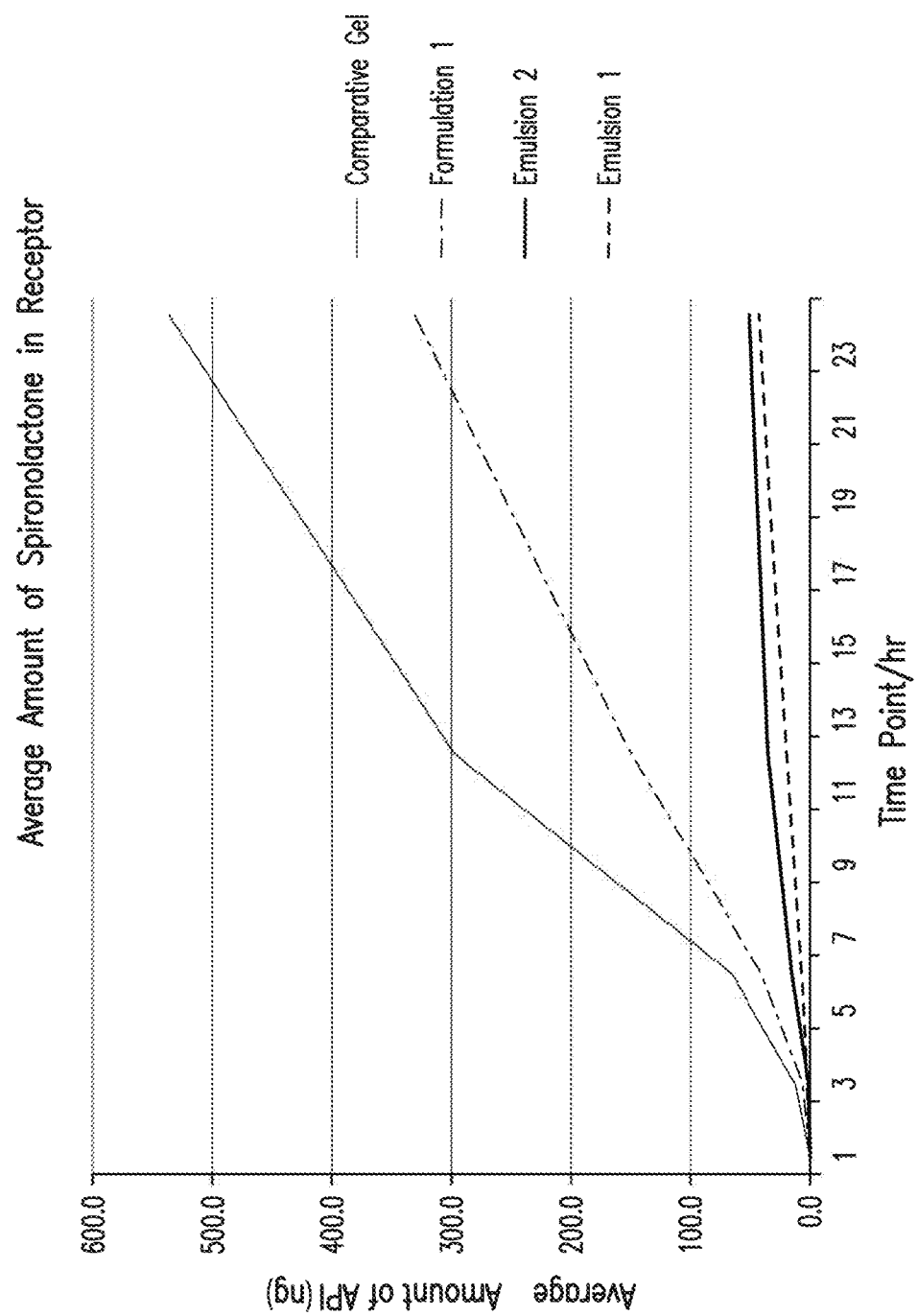
FIG. 11 shows the cumulative amount of spironolactone appearing in the receptor solution over 24 hours after a single 5.0 μl per cell (10 mg per cm$^2$ of skin tissue) for an exemplary aqueous suspension formulation (Formulation 1), Emulsion 1, Emulsion 2, and a Comparative Gel formulation (as described in further detail in Example 5).
Figure 12:
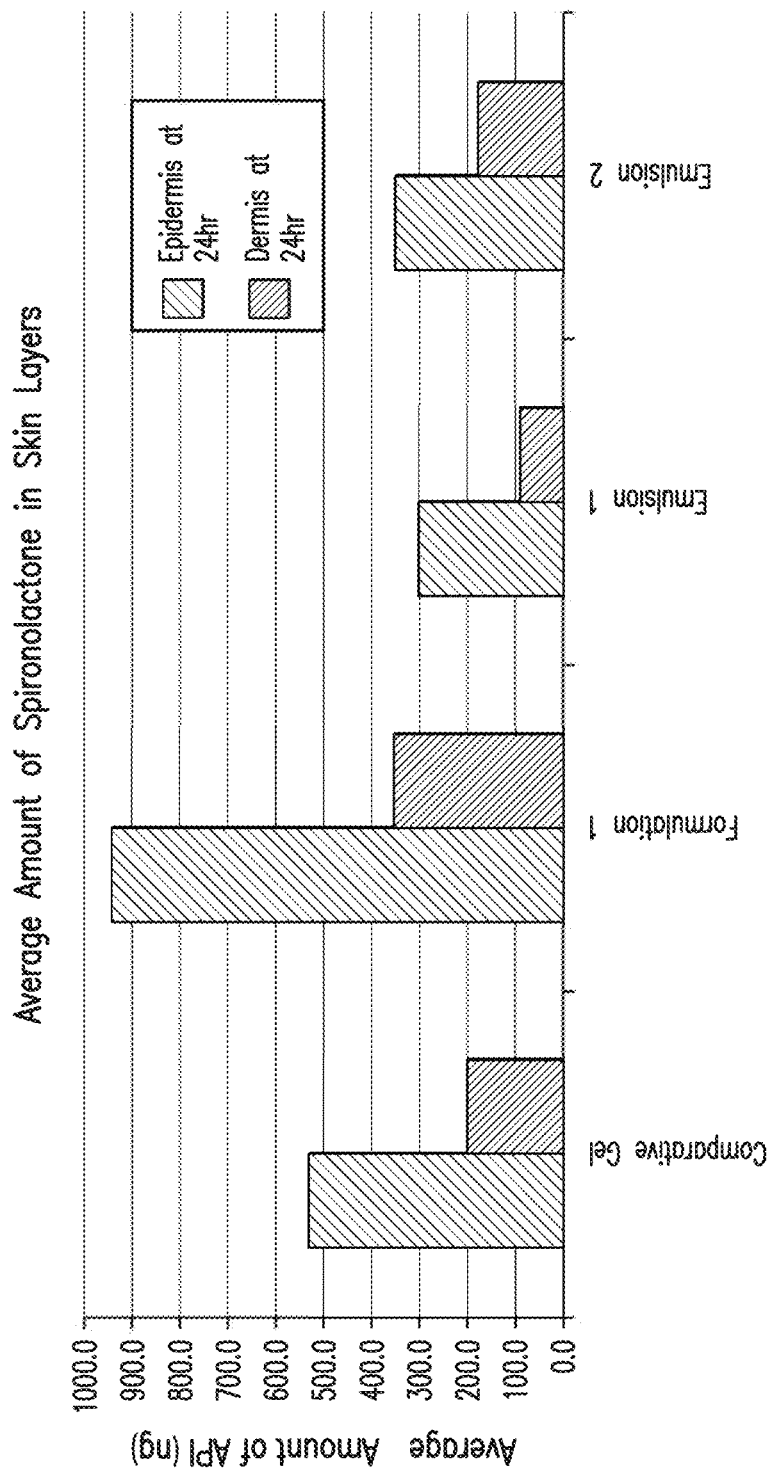
FIG. 12 shows the amount of spironolactone (ng) in the epidermis and dermis after 24 hours for the exemplary aqueous suspension formulation (Formulation 1), Emulsion 1, Emulsion 2, and a Comparative Gel formulation (as described in Example 5).

FIG. 11 illustrates the cumulative amount of spironolactone appearing in the receptor solution over 24 hours after a single 5.0 μl per cell (10 mg per $cm^2$ of skin tissue) for Formulation 1, Emulsion 1, Emulsion 2, and the Comparative Gel. In FIG. 11, each plotted value is the average of four separate pieces of excised human skin. FIG. 12 illustrates the amount of spironolactone (ng) in the epidermis and dermis after 24 hours for Formulation 1, Emulsion 1, Emulsion 2, and the Comparative Gel. As seen in FIG. 12 the comparative gel with 5% dissolved spironolactone delivered more spironolactone across excised human skin than the 5% spironolactone water suspension or either of the two emulsion formulations. However, significantly greater deposition of spironolactone into the epidermis (location of the infundibulum of the pilosebaceous unit) for the aqueous suspension is seen in FIG. 12 compared to the comparative gel having dissolved spironolactone or the silicone oil emulsions having submicron particles of suspended spironolactone. High levels of API in the epidermis and dermis indicates that spironolactone targets the pilosebaceous unit and has significantly greater follicular deposition from the aqueous suspension (D90<0.5 μm which is Formulation 1).

Example 6

A 5.0%-5.5% spironolactone suspension in water containing 0.05%-0.055% dioctyl sodium sulfosuccinate and 1.0-1.1% hydroxyl propyl cellulose was nano-milled to achieve the particle size distribution shown in FIG. 6. To this aqueous suspension different preservatives, thickening agents and ethanol were added to this aqueous suspension as shown in Table 5. Seven different formulations (S1-S7) were prepared as set forth in Table 5.

In vitro skin penetration testing (IVPT) was used to determine how rapidly the different formulations crossed excised human skin. Human cadaver skin was procured from two donors (Caucasian female age=44 abdomen skin dermatomed to an average thickness of 710 μm and Caucasian female age=48 abdomen skin dermatomed to an average thickness of 578 μm). Dermatomed skin was received frozen from a US tissue bank and stored at −20° C. until use. Skin was loaded onto vertical Franz cells having a 0.503 $cm^2$ (8 mm in diameter) diffusion area and a receptor chamber filled with 3.0 ml of 4% BSA in water containing 0.01% gentamicin sulfate thermostated at 32° C. Using a positive displacement pipette, 5 microliters of each formulation was dosed on each Franz Cell (10 mg per square centimeter of skin). Receptor solutions were analyzed using a validated LC-MS/MS (Kinetex C18, 5 μm, 2.1×50 mm column, Shimadzu LC20ADXR pumps and AB Sciex API 4000 Turbo Spray detector). The cumulative amount of spironolactone assayed in the receptor solution is the average of four replicate IVPT measurements.

To determine the levels of spironolactone retained in the epidermis and dermis 24-hours after dosing the skin, the skin surface was cleaned of any unabsorbed and unpenetrated spironolactone. This was accomplished by wiping the tissue surface with a Q-tip wetted with 1×PBS three times followed by two tape strippings. The epidermis (including the stratum corneum) was removed from the dermis and soaked in 4.0 ml of a DMSO/Acetonitrile (ACN) (50/50 v/v) mixture for overnight at room temperature using an orbit shaker. The remaining dermis layer was cut into small pieces and extracted with 4.0 ml of the DMSO/ACN mixture for overnight at room temperature using an orbit shaker. Extracts of the dermis and epidermis were analyzed using a validated LC-MS/MS (Kinetex C18, 5 μm, 2.1×50 mm column, Shimadzu LC20ADXR pumps and AB Sciex API 4000 Turbo Spray detector).

Figure 13:
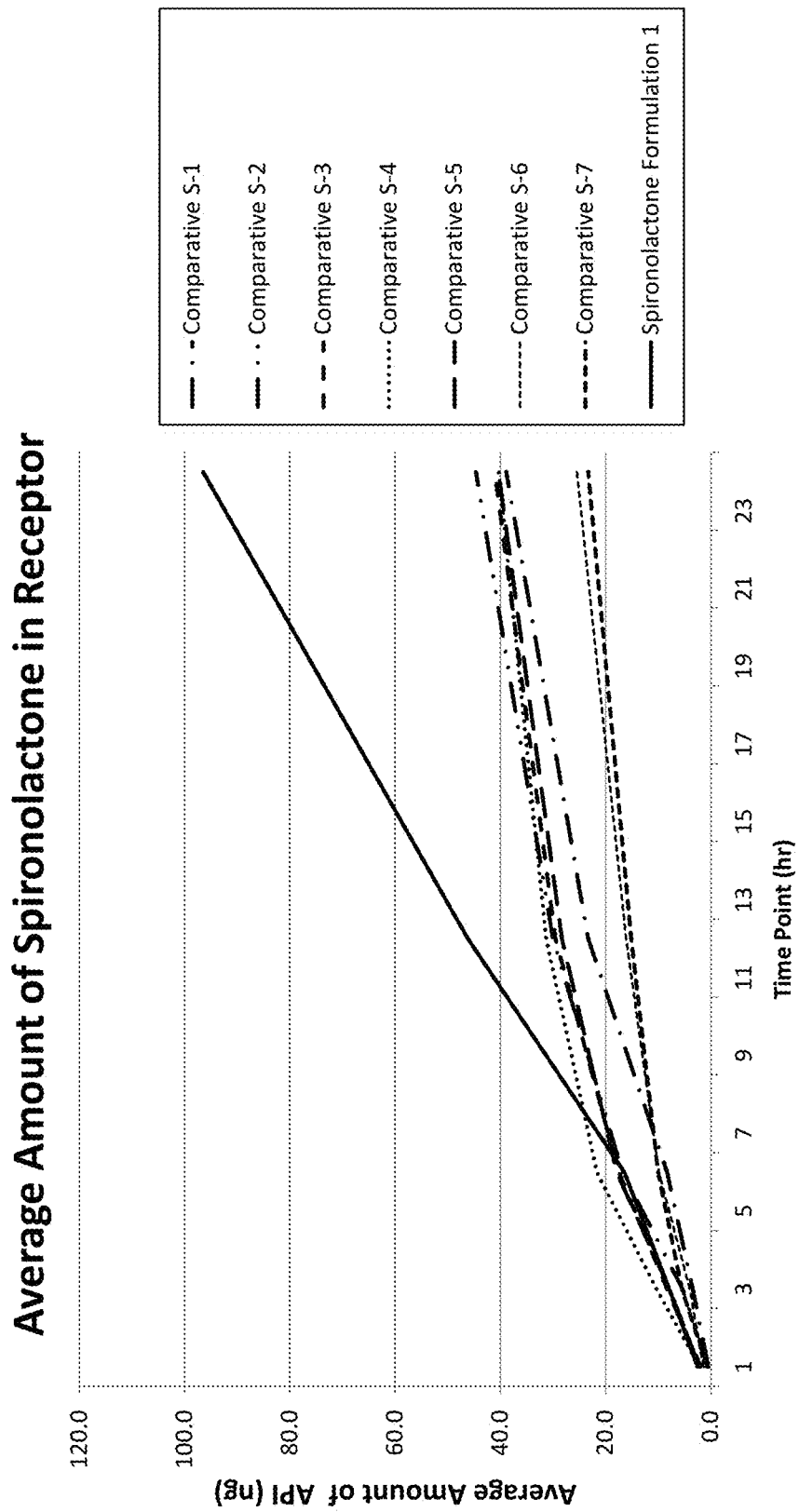
FIG. 13 shows the average amount of spironolactone appearing in the receptor solution over 24 hours after a single 5.0 μl per cell (10 mg per cm$^2$ of skin tissue) for eight exemplary formulations (S1-S7, described in Example 6, and Formulation 1, described in Example 4).

FIG. 13 illustrates the average amount of spironolactone appearing in the receptor solution over 24 hours after a single 5.0 μl per cell (10 mg per $cm^2$ of skin tissue) for S1-S7 and Formulation 1 (as described in Example 4). In FIG. 13,

TABLE 5

Composition of the Comparative Spironolactone (S) Aqueous Suspension Formulations.

Figure 14:
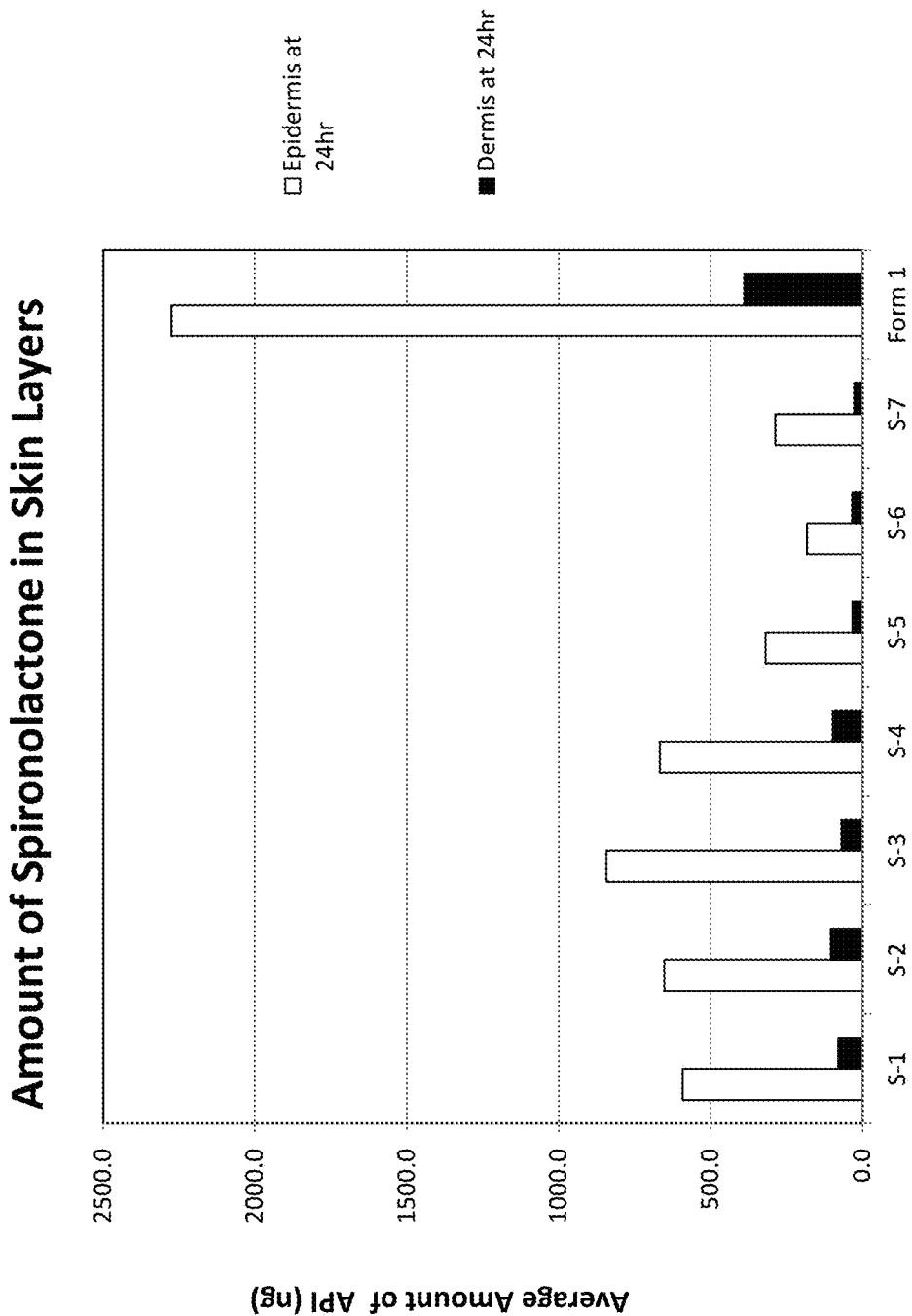
FIG. 14 shows the amount of spironolactone (ng) in the epidermis and dermis after 24 hours for eight exemplary formulations (S1-S7, described in Example 6, and Formulation 1, described in Example 4).

| Formulation Components | S-1 (% w/w) | S-2 (% w/w) | S-3 (% w/w) | S-4 (% w/w) | S-5 (% w/w) | S-6 (% w/w) | S-7 (% w/w) |
|---|---|---|---|---|---|---|---|
| Spironolactone | 4.98 | 4.94 | 4.94 | 4.90 | 4.89 | 5.00 | 4.93 |
| Methylparaben | 0.10 | 0.10 | 0.10 | — | 0.10 | — | 0.10 |
| Propylparaben | 0.01 | 0.01 | 0.01 | — | 0.01 | — | 0.01 |
| Phenoxyethanol | — | — | — | 1.00 | — | — | — |
| Benzyl Alcohol | — | — | — | — | — | 1.00 | — |
| Ethanol | — | — | — | — | — | 10.00 | — |
| Polysorbate 80 | — | — | — | — | 1.00 | — | — |
| Poloxamer 407 | — | — | — | — | — | — | 0.20 |
| Carbopol 974 | 0.30 | — | — | — | — | — | — |
| Hydroxypropyl cellulose | — | 1.00 | — | 1.00 | 1.00 | 1.00 | 1.00 |
| Hyaluronic Acid | — | — | 1.00 | — | — | — | — |
| Water containing 0.05-0.055% dioctyl sodium sulfosuccinate and 1.0-1.1% hydroxyl propyl cellulose | q.s. ad 100% | q.s. ad 100% | q.s. ad 100% | q.s. ad 100% | q.s. ad 100% | q.s. ad 100% | q.s. ad 100% | each plotted value is the average of four separate pieces of excised human skin. FIG. 14 illustrates the amount of spironolactone (ng) in the epidermis and dermis after 24 hours for S1-S7 and Formulation 1 (as described in Example 4). FIG. 14 shows that there was significantly greater deposition of spironolactone in the epidermis and dermis after topical dosing with an aqueous suspension (Formulation 1) compared with the seven other formulations (S1-S7) having the same particle size distribution set forth in FIG. 6. The data indicates that even minor modifications of adding a preservative or gelling agent inactivates the ability of suspended spironolactone to target the pilosebaceous unit.

The foregoing description has been presented for purposes of illustration and description. This description is not intended to limit the invention to the precise form disclosed. Persons of ordinary skill in the art will appreciate that modifications and substitutions of the basic inventive description may be made.

What is claimed is:

1. A method of treating alopecia areata in a subject in need thereof comprising:
    topically administering to the subject a pharmaceutical composition comprising: (a) a therapeutically effective amount of SHR0302 or a pharmaceutically acceptable salt thereof, wherein a primary particle size distribution of the SHR0302 is characterized by a D90 value of less than about 20 μm; and (b) a silicone selected from the group consisting of dimethicone and cyclomethicone.

2. The method of claim 1, wherein the SHR0302 is delivered to the pilosebaceous unit.

3. The method of claim 2, wherein the SHR0302 achieves dermal penetration of at least 1 mm in the subject.

4. The method of claim 3, wherein the pharmaceutical composition is a suspension.

5. The method of claim 1, wherein the composition comprises about 0.10% w/w to about 5% w/w of SHR0302 or a salt thereof.

6. The method of claim 5, wherein a primary particle size distribution of the SHR0302 is characterized by a D90 value of less than about 10 μm.

7. The method of claim 5, wherein a primary particle size distribution of the SHR0302 is characterized by a D90 value of less than about 5 μm.

8. The method of claim 5, wherein a primary particle size distribution of the SHR0302 is characterized by a D50 value of less than about 1.0 μm.

9. The method of claim 5, wherein a primary particle size distribution of the SHR0302 is characterized by a D10 value of less than about 0.50 μm.

10. A method of treating a hair loss condition in a subject in need thereof comprising:
    topically administering to the subject a pharmaceutical composition comprising: (a) a therapeutically effective amount of SHR0302 or a pharmaceutically acceptable salt thereof, wherein a primary particle size distribution of the SHR0302 is characterized by a D90 value of less than about 20 μm; and (b) a silicone selected from the group consisting of dimethicone and cyclomethicone.

11. The method of claim 10, wherein the hair loss condition is selected from the group consisting of alopecia, androgenic hair loss, hypotrichosis, and telogen effluvium.

12. The method of claim 11, wherein the SHR0302 is delivered to the pilosebaceous unit.

13. The method of claim 12, wherein the SHR0302 achieves dermal penetration of at least 1 mm in the subject.

14. The method of claim 13, wherein the pharmaceutical composition is a suspension.

15. The method of claim 10, wherein the composition comprises about 0.10% w/w to about 5% w/w of SHR0302 or a salt thereof.

16. The method of claim 15, wherein a primary particle size distribution of the SHR0302 is characterized by a D90 value of less than about 10 μm.

17. The method of claim 15, wherein a primary particle size distribution of the SHR0302 is characterized by a D90 value of less than about 5 μm.

18. The method of claim 15, wherein a primary particle size distribution of the SHR0302 is characterized by a D50 value of less than about 1.0 μm.

19. The method of claim 15, wherein a primary particle size distribution of the SHR0302 is characterized by a D10 value of less than about 0.50 μm.

* * * * *